United States Patent
Saló Darder

(10) Patent No.: US 10,213,360 B2
(45) Date of Patent: Feb. 26, 2019

(54) DIAGNOSTIC AND TREATMENT METHODS

(71) Applicant: MC HEALTH TECH S.L., Barcelona (ES)

(72) Inventor: Jordi Saló Darder, La Bisbal d'Empordà (ES)

(73) Assignee: MC HEALTH TECH S.L., Barcelona (ES)

( * ) Notice: Subject to any disclaimer, the term of this patent is extended or adjusted under 35 U.S.C. 154(b) by 624 days.

(21) Appl. No.: 14/764,163

(22) PCT Filed: Jan. 28, 2014

(86) PCT No.: PCT/EP2014/051643
§ 371 (c)(1),
(2) Date: Jul. 28, 2015

(87) PCT Pub. No.: WO2014/118187
PCT Pub. Date: Aug. 7, 2014

(65) Prior Publication Data
US 2016/0022530 A1   Jan. 28, 2016

Related U.S. Application Data

(60) Provisional application No. 61/757,839, filed on Jan. 29, 2013.

(51) Int. Cl.
*A61H 7/00*  (2006.01)
*A61H 9/00*  (2006.01)
*A61B 5/00*  (2006.01)

(52) U.S. Cl.
CPC ............. *A61H 9/0057* (2013.01); *A61B 5/45* (2013.01); *A61H 2205/02* (2013.01)

(58) Field of Classification Search
CPC ......... A61H 9/00; A61H 2205/00; A61B 5/04
See application file for complete search history.

(56) References Cited

U.S. PATENT DOCUMENTS

| 6,484,747 B2 * | 11/2002 | Bridgers | A61M 16/08 128/204.18 |
| 9,693,931 B2 * | 7/2017 | Salo Darder | A61H 37/00 |
| 2002/0007836 A1 * | 1/2002 | Weyergans | A61H 9/005 128/898 |

(Continued)

FOREIGN PATENT DOCUMENTS

| WO | WO2010056124 A1 | 5/2010 |
| WO | WO2011101388 A1 | 8/2011 |

OTHER PUBLICATIONS

Karandikar, Ninad MD, et al: "Kinetic Chains: A Review of the Concept and Its Clinical Applications", PM&R, Feb. 19, 2011, vol. 3, No. 8, p. 739-745, American Academy of Physical Medicine and Rehabilitation, Lexington, KY.

(Continued)

*Primary Examiner* — Garrett Atkinson
(74) *Attorney, Agent, or Firm* — Peter B. Scull; Hamilton, DeSanctis & Cha LLP

(57) ABSTRACT

The present invention relates to a method of diagnosing the primary lesions that give rise to a chronic condition or incorrect structure in myofascial units and associated structures in a human patient. The invention also relates to a method of therapeutic treatment of the diagnosed conditions, in particular by application of a variable vacuum stimulus.

10 Claims, 17 Drawing Sheets

(56) References Cited

U.S. PATENT DOCUMENTS

| | | | | |
|---|---|---|---|---|
| 2004/0106907 | A1* | 6/2004 | Liu | A61H 9/005 604/313 |
| 2005/0027218 | A1* | 2/2005 | Filtvedt | A61F 7/00 601/152 |
| 2005/0070405 | A1* | 3/2005 | Egger | A61H 9/005 482/78 |
| 2006/0206040 | A1* | 9/2006 | Greenberg | A61H 9/005 601/9 |
| 2006/0211958 | A1* | 9/2006 | Rosenberg | A61H 23/0236 601/9 |
| 2007/0208281 | A1* | 9/2007 | Brooks | A61H 9/005 601/6 |
| 2008/0009815 | A1* | 1/2008 | Grabenkort | A61M 1/0031 604/346 |

OTHER PUBLICATIONS

Teinold, Mike (Nov. 29, 2011), "The Problem with the Kinetic Chain Concept", MikeReinold.com, Retrieved from the Internet Mar. 27, 2014, from URL:http://www.mikereinold.com/2011/11/the-problem-with-the-kinetic-chain-concept.html, pp. 1-10.

Howitt, Scott: "The Weak Link", Canadian Chiropractor, Jun. 29, 2007, p. 24-25, Ontario, CA.

Cematec traumatologia (Oct. 24, 2012), "Multiterapia. CEMATEC. Traumatologia Barcelona", Youtube.com, Retrieved from the Internet Mar. 27, 2014, from URL:https://www.youtube.com/watch?v=oUqjJcSlEil2012.

Anonymus (2010) "OsteoSalut—Sokindex", Osteosalut.com, Retrieved from the Internet Mar. 27, 2014 from URL:http://www.osteosalut.com/aplicacion-del-metodo-salo-darder-en-casos-de-tunel-carpiano, Mar. 27, 2014.

International Search Report for PCT Application No. PCT/EP2014/051643, prepared by the European Patent Office, dated Apr. 14, 2014, 1-4 pages, Rijswijk, NL.

Spanish Language—Cematec traumatologia (Published Oct. 24, 2012), "Multiterapia. CEMATEC. Traumatologia Barcelona", Youtube.com, Retrieved from the Internet Mar. 27, 2014, from URL:https://www.youtube.com/watch?v=oUqiJcSlEil, XP002722363 (see detailed explanation in Non-English Certification Statement filed herewith).

English Translation—Cematec traumatologia (Published Oct. 24, 2012), "Multiterapia. CEMATEC. Traumatologia Barcelona", Youtube.com, Retrieved from the Internet Mar. 27, 2014, from URL:https://www.youtube.com/watch?v=oUqiJcSlEil, XP002722363 (see detailed explanation in Non-English Certification Statement filed herewith).

Spanish Language—Cematec traumatologia (Published Oct. 24, 2012), "Multiterapia. CEMATEC. Traumatologia Barcelona", Youtube.com, Retrieved from the Internet: Jul. 28, 2015, from URL:https://www.youtube.com/watch?v=oUqiJcSlEil. (see detailed explanation in Non-English Certification Statement filed herewith).

English Language—Cematec traumatologia (Published Oct. 24, 2012), "Multiterapia. CEMATEC. Traumatologia Barcelona", Youtube.com, Retrieved from the Internet: Jul. 28, 2015, from URL:https://www.youtube.com/watch?v=oUqiJcSlEil. (see detailed explanation in Non-English Certification Statement filed herewith).

Spanish Language—Cematec traumatologia (Published Oct. 24, 2012), "Multiterapia. CEMATEC. Traumatologia Barcelona", Youtube.com, Retrieved from the Internet: Aug. 17, 2015, from URL:https://www.youtube.com/watch?v=oUqiJcSlEil. (Slide by slide representation of video, see detailed explanation in Non-English Certification Statement filed herewith).

English Translation—Cematec traumatologia (Published Oct. 24, 2012), "Multiterapia. CEMATEC. Traumatologia Barcelona", Youtube.com, Retrieved from the Internet: Aug. 17, 2015, from URL:https://www.youtube.com/watch?v=oUqiJcSlEil. (Slide by slide representation of video, see detailed explanation in Non-English Certification Statement filed herewith).

Spanish Language—Anonymous: (2010) "OsteoSalut—Sokindex", Osteosalut.com, Retrieved from the Internet Mar. 27, 2014 from URL:http://www.osteosalut.com/aplicacion-del-metodo-salo-darder-en-casos-de-tunel-carpiano. XP002722364 (see detailed explanation in Non-English Certification Statement filed herewith).

English Translation—Anonymous: (2010) "OsteoSalut—Sokindex", Osteosalut.com, Retrieved from the Internet Mar. 27, 2014 from URL:http://www.osteosalut.com/aplicacion-del-metodo-salo-darder-en-casos-de-tunel-carpiano. XP002722364 (see detailed explanation in Non-English Certification Statement filed herewith).

Spanish Language—OsteoSalut (Product page), Osteosalut.com, Retrieved from the Internet Jul. 28, 2015, from URL:http://www.osteosalut.com/aplicacion-del-metodo-salo-darder-en-casos-de-tunel-carpiano (see detailed explanation in Non-English Certification Statement filed herewith).

English Translation—OsteoSalut (Product page), Osteosalut.com, Retrieved from the Internet Jul. 28, 2015, from URL:http://www.osteosalut.com/aplicacion-del-metodo-salo-darder-en-casos-de-tunel-carpiano (see detailed explanation in Non-English Certification Statement filed herewith).

\* cited by examiner

Position 0     Flexion     Extension

Position 0     Lateral inclination (right)     Lateral Inclination (Left)

Position 0     Left rotation     Right rotation

DIAGNOSTIC AND TREATMENT METHODS

FIELD OF THE INVENTION

The present invention relates to a method of diagnosing the primary lesions that give rise to a chronic condition or incorrect structure in myofascial units and associated structures in a human patient. The invention also relates to a method of therapeutic treatment of the above-mentioned conditions.

BACKGROUND

The diagnosis of chronic conditions or incorrect structures in myofascial units and associated structures in a human patient usually involves the elaboration of the medical history or anamnesis of the human patient by gathering information through questioning by a physician either of the patient or of other people who know the patient and can give suitable information. The medically relevant complaints reported by the patient or others familiar with the patient are referred to as symptoms. This information is complemented by the determination of clinical signs, which are ascertained by direct examination on the part of medical personnel. The information obtained in this way enables the physician to form a diagnosis and treatment plan.

Traditionally, once the lesion or incorrect structure has been identified the treatment plan focuses on restoring the normal function of the structure primarily, although not exclusively, by direct interaction with the incorrect structure where the lesion is located.

Although this strategy provides relief in a number of instances it has been reported that not all patients respond adequately to the treatment of the diagnosed lesion or respond partially or respond to treatment but relapse once treatment is finished or shortly afterwards.

DESCRIPTION OF THE INVENTION

The inventors have now surprisingly found that, limiting the treatment to the restoring of the normal function of the structure associated with the symptoms reported by the patient, provides suboptimal results and as such, they have developed a new diagnostic technique that allows identifying the causes or primary lesions that give rise to the chronic condition or incorrect structure (such as scoliosis, kyphosis, lordosis or limb dysmetria) that is the primary motivation for the patient's quest for medical attention.

In a first aspect of the present invention the new diagnostic technique (which the inventors have named Saló-Darder Methods or SD Method) is based on the finding that individual myofascial units (and their associated joint articulations) form the links in a so-called myofascial chain. There are several myofascial chains which originate in the foot and go to the cranium.

It is hypothesized that the state of stress in tissues (muscles, fascias, joints, nerves, blood and lymph vessels, organs, viscera), traumatic injury to these, or degenerative processes bring about retraction (muscular system) and adherences (fascial system), and/or scarring fibrosis which, in turn, cause limitation of movement (muscular, articular and fascial), as well as pain and inflammation (muscular, articular and fascial), and may be linked to stenosis in the aponeurosis of the vascular and nervous systems.

Faced with these limitations of movement, the individual makes unconscious muscular-articular-fascial compensations. These compensations involve the intervention of tissue (muscles, fascias and articular joints) tensional chains.

It has been found that when one of the links (at any point of the chain) comes under tension, a tensional chain is initiated. The link at which the tensional chain begins is called the "primary lesion". The primary lesion will, in turn, tense all of the subsequent myofascial units (links) and articular joints in sequential order.

The provoked tension along the myofascial chain (starting from the primary lesion) will create the so called "tensional chain". This can lead to incorrect biomechanical compensations in the body, leading to tension in the antagonistic muscles of the affected tensional chain, which will provoke a symptomatic lesion. This symptomatic lesion tends to be the object of the consultation with a practitioner (such as a Traumatologist, a Physiotherapist or a Manual Therapist). This symptomatic lesion is most often found at the end of the tensional chain distal from the primary lesion and it may occur as:

1. Muscular and fascial pain, inflammation and limitation of the joint articulation movement, any other type of pain (reason for consultation) distal from the initial pathological process (primary lesion).
2. Stenosis in the vascular, lymphatic and nervous systems.

The SD method has identified eight potential tensional myofascial chains (and one local myofascial chain related to the scapula) which are described in detail below.

Based on the above premises, when a patient explains the reason for his visit (usually localized pain) to the practitioner, the practitioner must rule out an injury chain that causes this pain. Otherwise, the treatment applied to the affected area may be insufficient and cause a recurrence, due to the persistence of the injury chain.

Consequently, the principle of the Saló-Darder diagnostic system is that it is necessary to locate the injury chain that might be responsible for causing the injury giving rise to the visit and establish which tissues (muscles, fascia and joints) of the chain are affected by the primary lesion.

To identify the existence of an injury chain, the practitioner must determine.

1. Firstly, which kinetic chain dominates the affected area where the patient is reporting symptoms or which is identified by the practitioner as the affected area.
2. Secondly, after locating the dominant kinetic chain, the practitioner must identify which link (myofascial unit) has given rise to the injury chain, known as the "primary lesion in the injury chain" (or simply, the "primary lesion" or "site of origin").

The primary lesion exerts dominance over the other lesions and is the key lesion to be treated in the first place. The SD Method lays down a general rule for identifying the primary lesion in each injury chain: of all the myofascial units affected, the primary lesion will be the one in the most caudal position (i.e., of all the links affected, the one nearest the foot will be the one giving rise to the injury chain). This primary lesion must then be treated to restore it to its normal condition.

In a second aspect of the present invention, a method of treatment is provided comprising the following steps a) the practitioner identifies the primary lesion following the method described herein, b) the practitioner treats the primary lesion c) the practitioner re-evaluates the injury chain and, d) in the event that symptoms persist the practitioner identifies the new primary lesion (a different one since the first lesion will have been normalised) and eventually treats the newly identified lesion. This process may be repeated as many times as necessary. Nevertheless, in order to avoid the need of repeated re-evaluations after every single treatment step, the practitioner may alternatively decide to treat the complete injury chain starting from the primary lesion (the lesion in the most caudal position in the injury chain) and continuing with the treatment of the rest of the myofascial units in the injury chain in the foot to head (caudal to cranial) direction. Thus, in an alternative embodiment of the present invention the method of treatment comprises the following steps a) the practitioner identifies the primary lesion as hereinabove described and b) the practitioner treats the complete injury chain starting from the primary lesion (the lesion in the most caudal position in the injury chain) and continuing with the treatment of the rest of the myofascial units in the injury chain in the foot to head (caudal to cranial) direction.

In a third aspect of the present invention a method of treatment is provided whereby lesions are treated using mechanical devices for the application of localized vacuum/pressure stimulus of variable intensity, such as a series of vacuum pulses, to the body areas to be treated.

DETAILED EXPLANATION OF THE FIGURES

Figure 10:
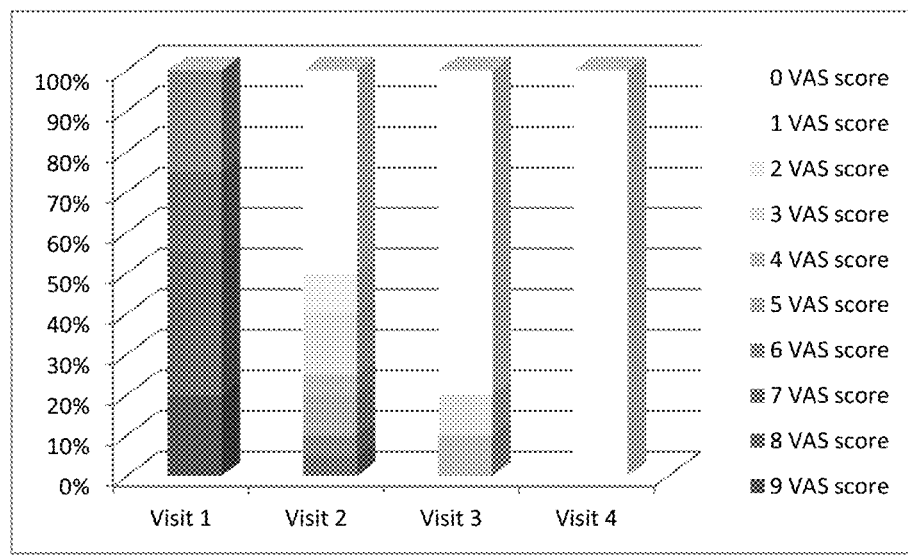

FIG. 10 the distribution of patients according to their VAS score (Visual Analogue Scale) at the first visit/treating session, the second visit/treating session, the third visit/treating session and the forth visit/treating session.

Figure 11:
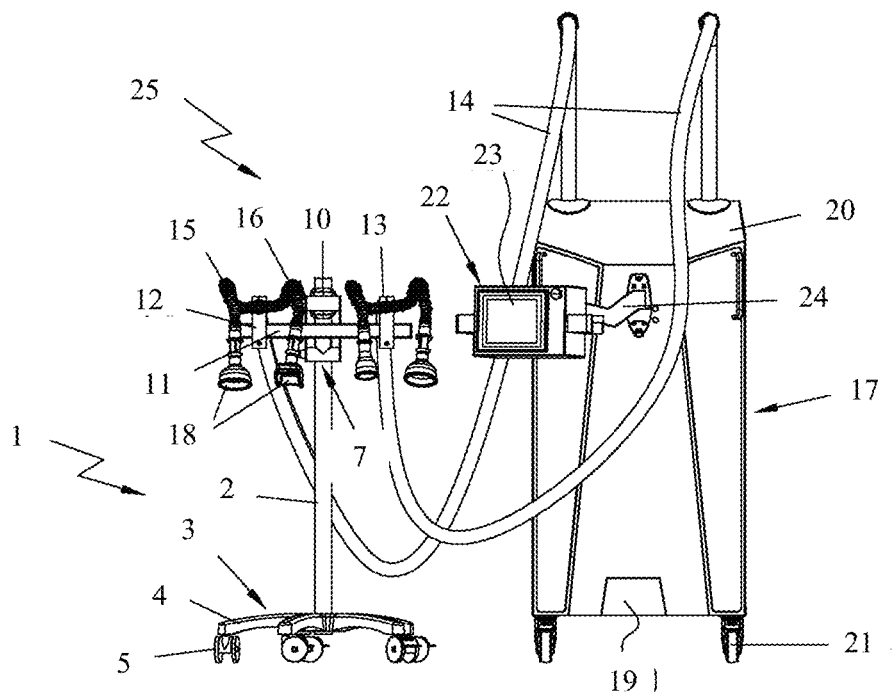
Figure 12:
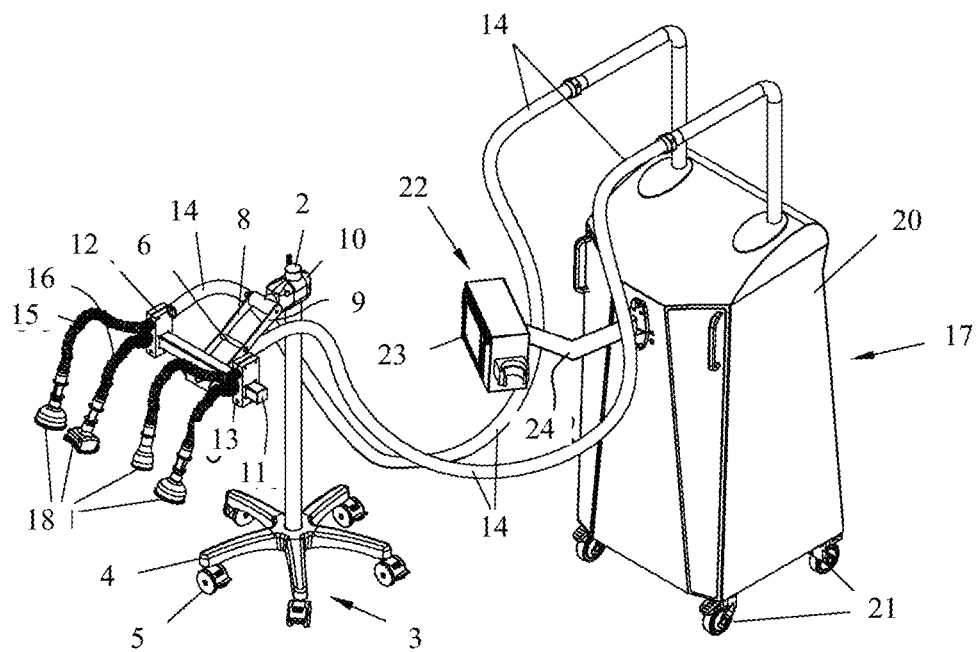

FIG. 11 and FIG. 12 show an apparatus as described in WO 2011/101388 which is used to carry out the treatments described in examples 2 to 8 of the present application.

Figure 13:
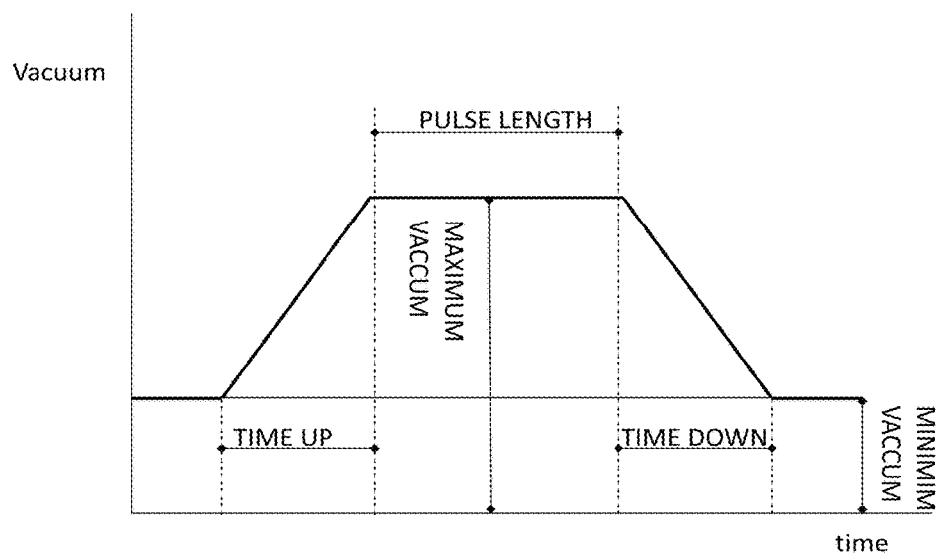

Numerals 1 to 25 appearing in FIG. 11 and FIG. 12 have the following meanings:
1 support device
2 support member
3 lower base portion
4 supporting arms
5 wheel carpet caster
6 transverse reinforcing spacer
7 arm structure
8 and 9 parallel arms
10 connecting member
11 carrying bar
12 and 13 hose connectors
14, 15 and 16 air inlet hoses
17 suction machine
18 applicators
19 suction means
20 housing
21 wheels
22 control means
23 display screen
24 mount arm
25 treatment assembly FIG. 13 illustrates the shape of a single vacuum pulse according to a preferred embodiment of the present invention (described in pages 34 to 35).

Figure 14:
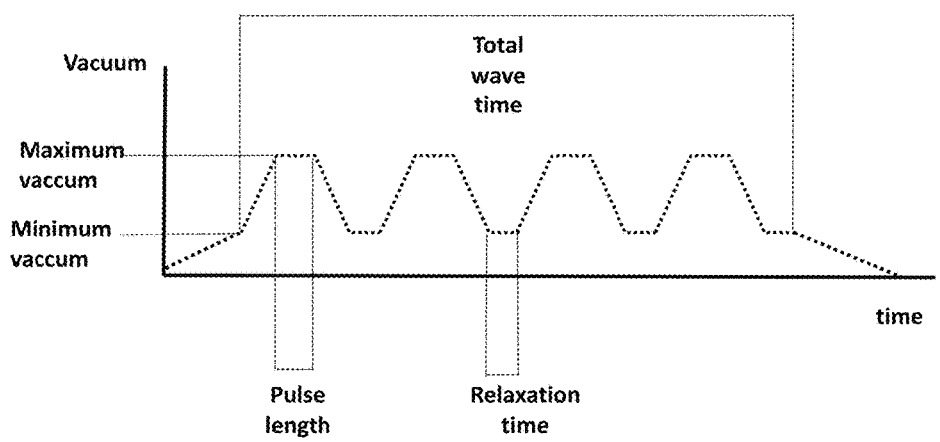

FIG. 14 shows a pulsating vacuum pattern (vacuum wave) applied in a preferred embodiment of the present invention (described in pages 34 to 35) which comprises a series of pulses as shown in FIG. 13.

Figure 15:
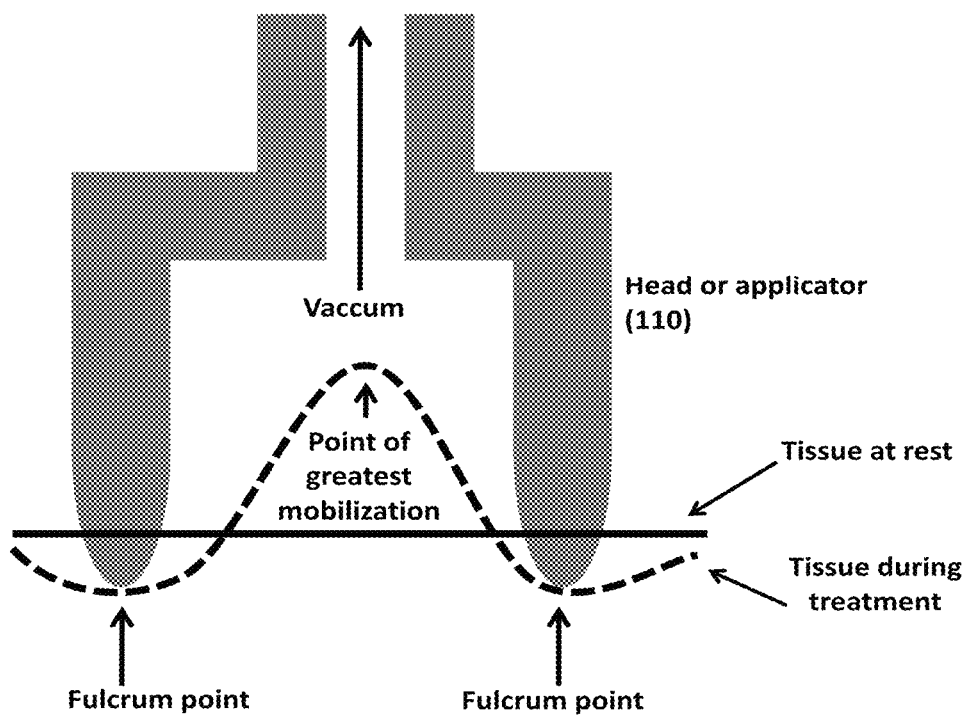

FIG. 15 illustrates an applicator (110) of the apparatus when brought in contact with a patient's skin in the course of a treatment according to the present invention.

Figure 16:
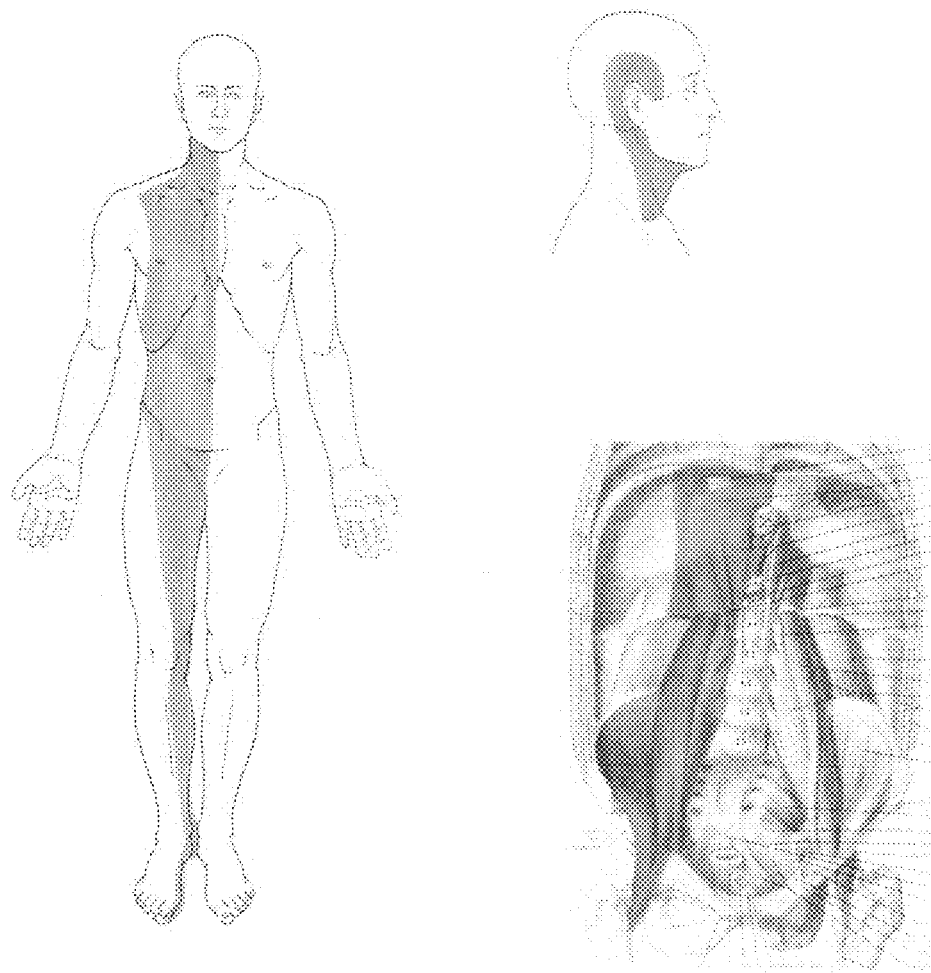

FIG. 16 shows in a schematic representation of the human body the location of the RMTC chain. The position of the LMTC is identical but on the contralateral side of the body.

Figure 17:
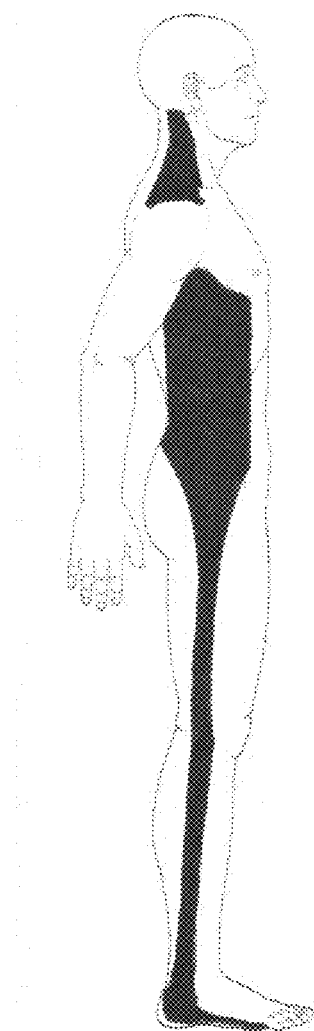

FIG. 17 shows in a schematic representation of the human body the location of the RLTC chain. The position of the LLTC is identical but on the contralateral side of the body.

Figure 18:
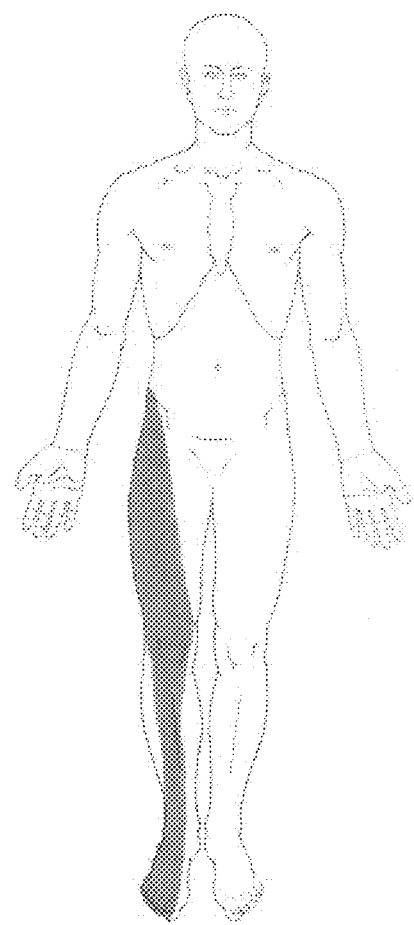

FIG. 18 shows in a schematic representation of the human body the location of the RATC chain. The position of the LATC is identical but on the contralateral side of the body.

Figure 19:
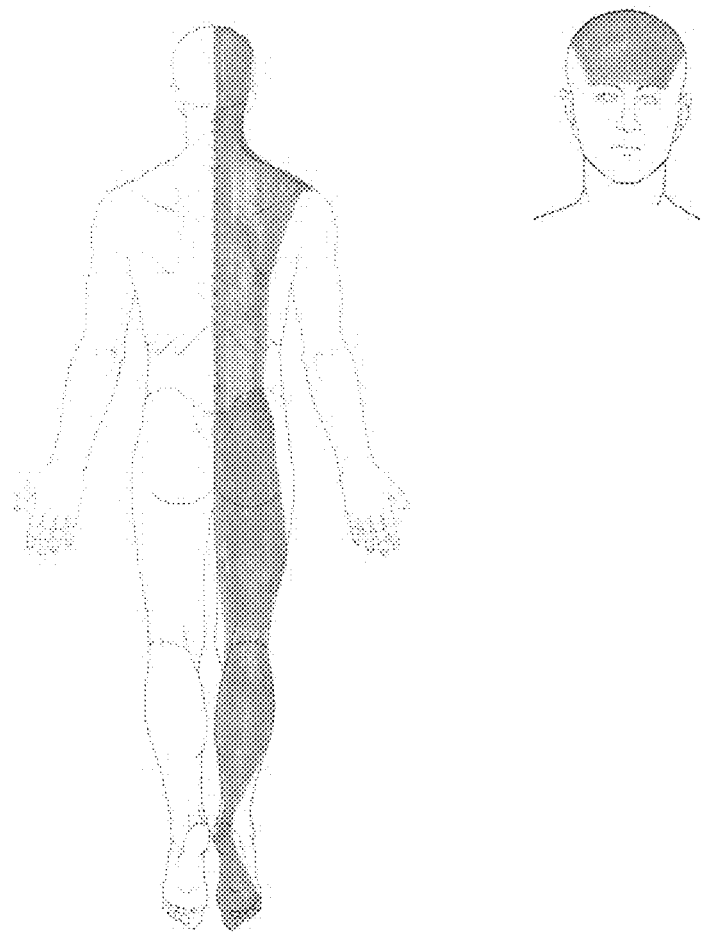

FIG. 19 shows in a schematic representation of the human body the location of the RPTC chain. The position of the LPTC is identical but on the contralateral side of the body.

Figure 20:
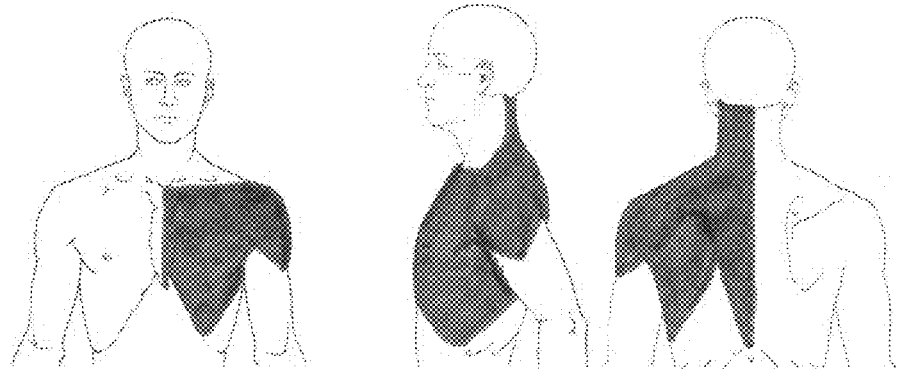

FIG. 20 shows in a schematic representation of the human body the location of the TSTC chain.

Figure 21:
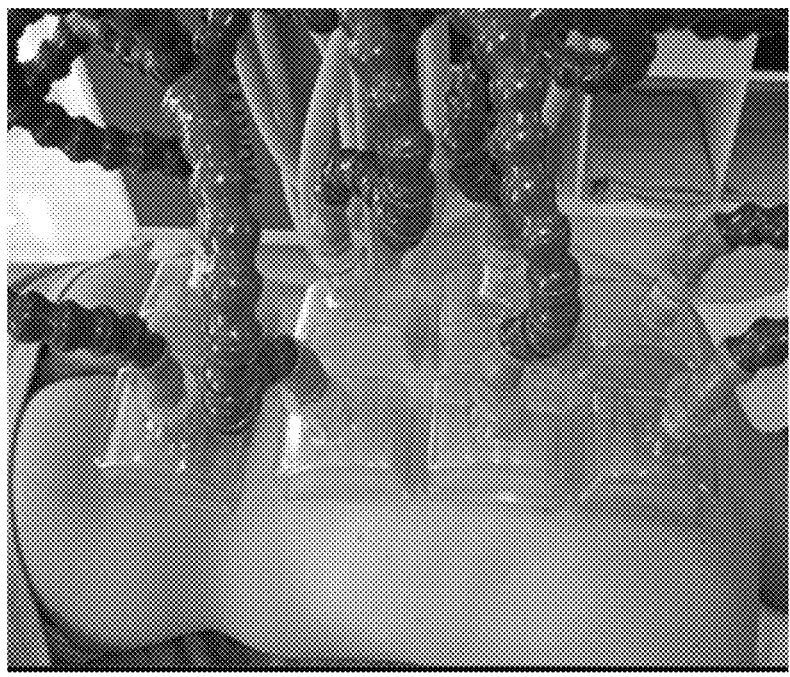
Figure 22:
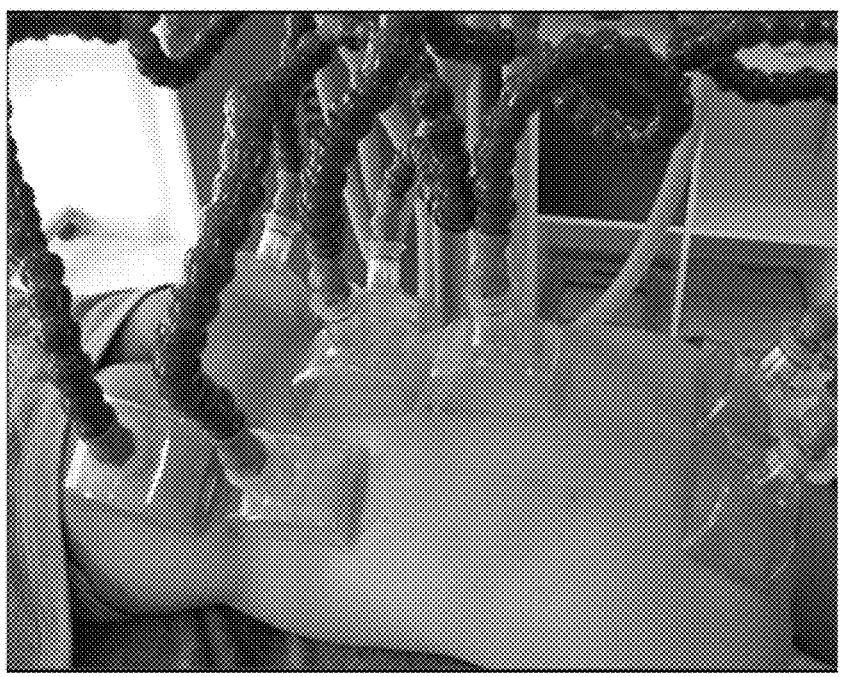

FIG. 21 and FIG. 22 show the positioning of the suction heads (applicators) during the first step of the treatment described in Example 2.

Figure 23:
Figure 24:
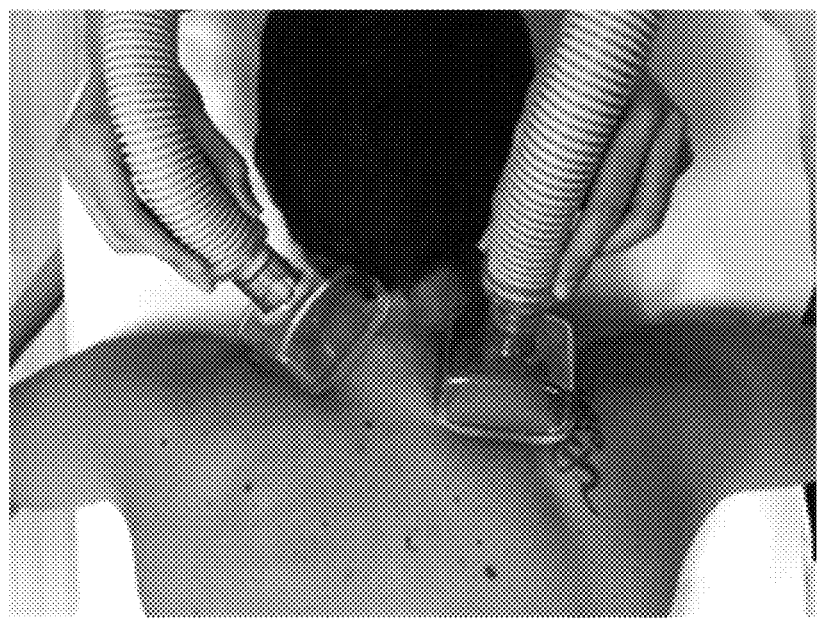

FIG. 23 and FIG. 24 show the positioning of the suction heads (applicators) during the second step of the treatment described in Example 2.

Figure 25:
Figure 26:
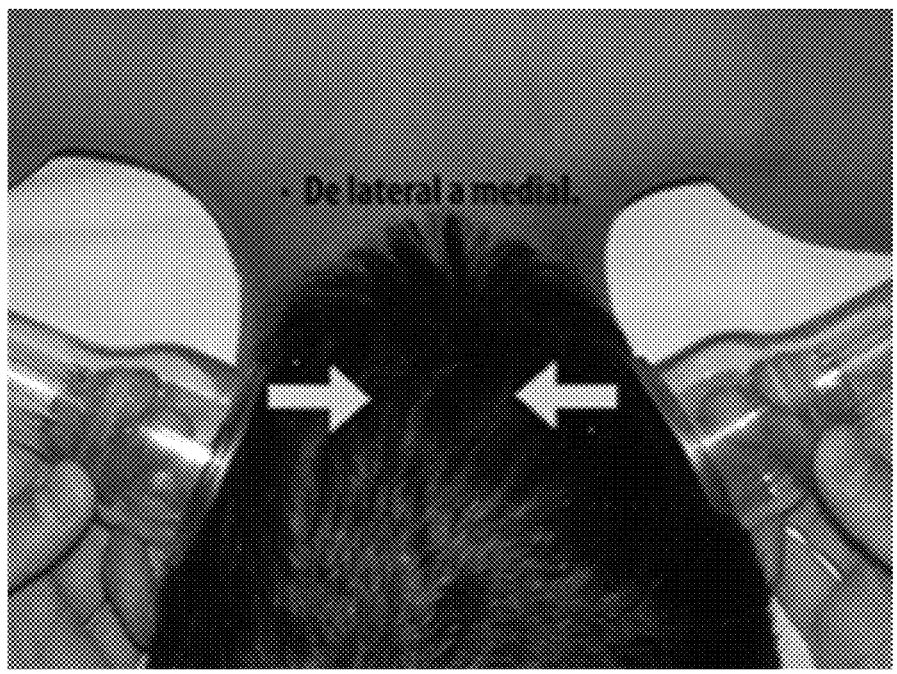

FIG. 25 and FIG. 26 show the positioning of the suction heads (applicators) during the third step of the treatment described in Example 2.

Figure 27:

FIG. 27 shows the positioning of the suction heads (applicators) during the fourth step of the treatment described in Example 2.

Figure 28:

FIG. 28 show the positioning of the suction heads (applicators) during the last step of the treatment described in Example 2.

Figure 29:
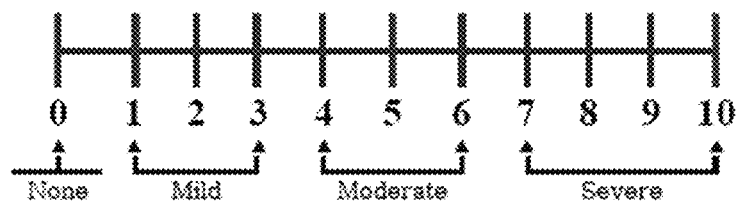

FIG. 29 shows the VAS score (Visual Analogue Scale) used for the evaluation of pain.

Figure 30:
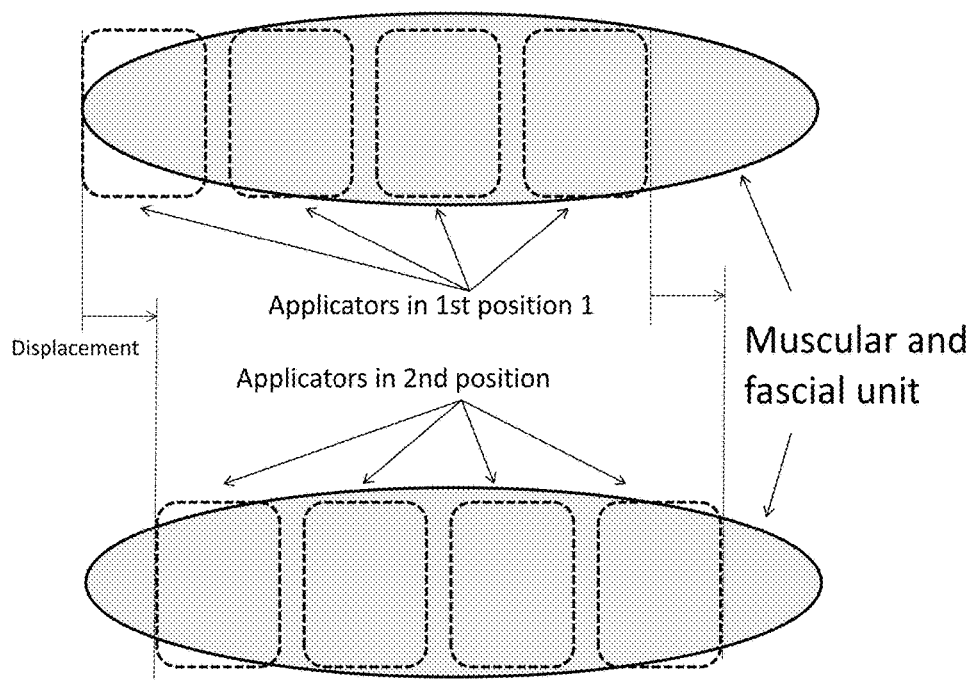

FIG. 30 illustrates how the vacuum applicators may be displaced during the treatment of a myofascial unit to cover the complete extension of said myofascial unit.

DETAILED EXPLANATION OF THE DIAGNOSTIC METHOD

The SD Method establishes that individual myofascial units (and their associated joint articulations) make up each of the links in a myofascial chain. The chain originates in the foot and goes to the cranium.

When one of the links (at any point of the chain) comes under tension, a tensional chain is initiated. The link at which the tensional chain begins is called the "primary lesion". The primary lesion will, in turn, tense all of the subsequent myofascial units (links) and articular joints in sequential order.

The provoked tension along the myofascial chain (starting from the primary lesion) will create the so called "tensional chain". This can lead to incorrect biomechanical compensations in the body; leading to tension in the antagonistic muscles of the affected tensional chain, which will provoke a symptomatic lesion (this tends to be the object of the consultation with a practitioner (such as a Traumatologist, a Physiotherapist or a Manual Therapist). This symptomatic lesion is most often found at the end of the tensional chain distal from the primary lesion, it may present as:
 a) muscular and fascial pain,
 b) inflammation and limitation of the joint articulation movement,
 c) any other type of pain (reason for consultation) distal from the initial pathological process (primary lesion).
 d) stenosis in the vascular, lymphatic or nervous system.

The SD method has identified eight potential tensional myofascial chains and one local myofascial chain related to the scapula.

The potential tensional myofascial chain (from now on TC) originates from the feet and inserts into the pelvis. At the pelvis, the TC continues or subdivides into two TC and terminates in the cervical vertebrae and cranium region.

As mentioned before the SD method has identified nine potential tensional myofascial chains: four Tensional Chains including the lower right limb, four including the lower left limb and one related to the scapula. Each chain receives a different name according to its topography and route:
 1. Right Medial Tensional Chain (RMTC)
 2. Left Medial Tensional Chain (LMTC)
 3. Right Lateral Tensional Chain (RLTC)
 4. Left Lateral Tensional Chain (LLTC)
 5. Right Anterior Tensional Chain (RATC)
 6. Left Anterior Tensional Chain (LATC)
 7. Right Posterior Tensional Chain (RPTC)
 8. Left Posterior Tensional Chain (LPTC)
 9. Transverse Scapula Tensional Chain (TSTC)

The positions of the above-mentioned tensional chains (only those on the body's right hand side) are illustrated in FIGS. 16 to 20. A detailed description of the above-mentioned Tensional Chains is found in the section headed "SD Tensional Chains"

SD (Saló-Darder) Tensional Chains
Medial Tensional Chains (RMTC and LMTC):
From Foot to Knee The Left and Right Medial Tensional Chains (LMTC and RMTC) comprise the deep posterior compartment of the lower leg, where we find the flexor hallucis longus, flexor digitorum longus, posterior tibialis and the fascias of these muscles, the artery and veins of the posterior tibialis, the tibial nerve, and the peroneal artery and vein. The superficial fascia (connective tissue of the dermis and the hypodermis), the saphenous nerve and vein, and the medial part of the superficial posterior compartment of the lower leg, also form part of the MTCs. Approximately one fifth of the medial fibres of the soleus and its fascia, and the medial fibres of the medial head of the gastrocnemius and its fascia also forms part of these tensional chains.

The MTCs originate at the foot, in the fascial and tendinous insertions of the muscles which make up the medial compartment of the lower leg, it continues up through the medial border of the tibia, inserts into the superficial and deep posterior fascia on the medial border of the tibia and merges with the periosteum. This fascia is reinforced by the aponeurotic expansions of the tendons of the sartorius, semitendinosus and gracilis muscles in the superior medial compartment of the tibia (pes anserinus).

When the MTCs are tensioned at the foot level the following may occur:
 They may alter the correct neurodynamic of the tibial nerve, through its passage in the deep posterior compartment of the flexor muscles. This tension subjects the nerve to compression and may cause mild neural stenosis. Although this stenosis is generally asymptomatic it creates abnormal afferent and efferent biofeedback reflexes in the endings of the calcaneal nerve, medial plantar nerve and lateral plantar nerve. Said process facilitates plantar fasciitis or calcaneal spurs; both of which are difficult to resolve without previously resolving the neurodynamic dysfunction.
 A primary lesion in the MTCs can generate sustained tension (mainly asymptomatic) at the flexor retinaculum of the foot; this increased tension can generate the effects of stenosis in the tarsal tunnel.
 Increasing the coaptation of all articular foot joints, limiting their movement and facilitating degeneration and painful articular processes.
 Pain (tendinous, synovial, neural, periosteal, retinacular or vascular) frequently appears in the area underlying the flexor retinaculum.
 Manifestation of tension in the MTCs may be caused by a foot with lax ligaments (pronated hind foot and mid foot in dynamic movement). The dynamics of the foot can generate overuse of the internal chain.
 Increasing tension in the tarsal tunnel may lead to stenosis around the underlying structures (tendinous sheath and tibial nerve) and may lead to altered biofeedback to the plantar and calcaneal nerves, both at afferent and efferent level.
 It may favour a calcaneal varus.
 Pronation in dynamic movement of the hind and mid foot generates an overuse of the MTCs and puts the whole of the MTCs in tension up to the pelvis.
 Calcaneal spurs and plantar fasciitis (possible irritation of the plantar nerve and of the calcaneal nerve in the tarsal tunnel).
 From Knee to Pelvis At the level of the pes anserinus the MTCs connect to the posterior Tensional Chains (RPTC and LPTC, to be described later) via the semitendinosus muscle.

The MTCs connect to the medial connective tissue structures of the knee (medial collateral ligament, meniscus medial, articular capsule, patellar tendon, medial patellar retinaculum, the patella and the local periosteum) via the aponeurotic extensions of the tendons inserted in the pes anserinus, and the extensions from superficial and deep compartment of the lower leg and the tibial periosteum.

The MTCs continue their path upwards from the medial compartment of the knee, pes anserinus region (gracilis and sartorius) and the adductor tubercle on the medial condyle of the femur. The aponeurotic expansions of the adductor magnus, sartorius and gracilis muscles connect with the medial articular capsule and greatly influence medial movement of the articular joint, the meniscus, the internal collateral ligament and the medial patellar retinaculum.

The MTCs goes up through the fascial compartments of the adductors. This network of fascias extends from the adductor tubercle to the linea aspera (medial lip) and up to the lesser trochanter, reaching the ischiopubic ramus, the supra pubic region and the inguinal ligament. On a muscular level, the MTCs are formed by the gracilis, sartorius, adductor magnus, adductor longus, adductor brevis, pectineus and their respective fascias. The blood vessels and nerves local to this region (great saphenous vein, femoral artery and vein, obturator nerve, saphenous nerve and medial branches of the femoral nerve which control the adductor muscles) form part of the MTCs.

The MTCs at the ischiopubic ramus and the fascias of the adductors have elongations which interconnect to the local periosteum and to the perineal fascia; this fascia covers the muscles that make up the female and male perineum (anterior pelvic diaphragm). The perineal fascias interconnect with the different fascias in the region through the aponeuroses. Connections to note in these fascia include the aponeurosis of the levator ani muscle, urethral sphincter muscle, retrovesical or retroprostatic fascia, prostate, rectum, vagina, seminal vesicle, bulbourethral glands (Cowper's gland), greater vestibular gland, penis, scrotum, retropubic fascia, bladder, and finally the fascias of the small blood vessels and nerve branches.

Tension in the MTCs have a major impact on the pelvic diaphragm and the perineum: it can compromise its functioning, causing all class of problems in pelvic viscera as well as in local blood vessels and nerves branches.

When the MTCs are tensioned at the knee level the following may occur:
  Coaptation of the medial portion of the articular joint.
  Limitation in medial and lateral rotation of the tibia with respect to the femur.
  Increased tension in the medial compartment. This will subsequently cause dysfunction in the vascular system due to stenosis; altering the mechanisms of the haemodynamics of the articular joint.
  Tension on the medial patellar retinaculum generates medial displacement of the patella when the knee is flexed.
  Increased thickness and sensibility of the medial collateral ligament. The cause resides in an excessive demand on the adductor magnus: this forces adduction from the internal femoral condyle, which exercises a stress on the medial portion of the knee, this in turn causes thickening of the medial collateral ligament.
  Early degeneration of the joint articulation. The most important causes being medial articular joint coaptation generated by the MTCs, limited joint movement, haemodynamic deficit due to vascular stenosis and limited movement of the medial meniscus.
  The MTCs facilitate meniscal pathologies of the medial meniscus, due to tension exercised on the medial articular joint capsule. This produces thickening of the medial collateral ligament and a limitation of the movement of the tibia with respect to the femur. All this generates a state of chronic suffering, both symptomatic and asymptomatic; it can cause spontaneous rupture to or increase degenerative changes in the meniscus.
  Tension in the MTCs may be the cause of many types of knee pain.
  Producing non-specific knee pain. The saphenous nerve forms part of the MTCs. Commonly, when the MTCs are in tension, the adductors and fascias compress the saphenous nerve creating abnormal afferent and efferent biofeedback on the medial compartment of the knee. This generates pain and hyperaesthesia.
  Pain in the medial area of the knee is common once tension in the MTCs has been established. The pain may present in any one of the structures at that site: patella, meniscus, patellar retinaculum lateral and medial, ligament, capsule, tendon insertion, local nerves etc.
  The femoral artery and vein pass through the hiatus of the adductor magnus. Tension in the MTCs may compromise the hiatus and can affect blood vessel functioning.
  Fluid retention. The MTCs present numerous foramens for the great saphenous vein, and also for small venous vessels and lymphatic ducts. When tension is established in the MTCs it may compromise venous return and lymphatic drainage.

When the MTCs are tensioned at the pelvis level the following may occur:
  The MTCs increases coaptation and limits coxofemoral movement, facilitating onset of degenerative articular joint processes.
  Compromised saphenous vein hiatus, due to its dependence on the laxity of the medial compartment. When tension exists in a MTC there may be a mild or severe stenosis of the saphenous vein in its hiatus. The most common symptoms depend on the seriousness of the stenosis; ranging from slow and progressive fluid retention in the lower limb to the appearance of small or large varicose veins.
  Generates a contralateral pelvic tilt with ipsilateral rotation. For example, tension in the right side generates a left tilt of the pelvis associated with a right rotation. This tilt is the cause of many pelvic and lumbar scolioses.
  Tension in the MTCs generates iliac anteversion. The hamstrings (biceps femoris, semimembranosus and semitendinosus) are put under tension as they are antagonists (they cause retroversion).
  The MTCs house the superior and inferior inguinal ganglions. When the cribriform fascia comes under tension, it causes stenosis in the lymphatic ducts, thereby diminishing their efficiency.

When the MTCs are tensioned at the perineum level the following may occur:
  Urinary Incontinence (UI) due to dysfunction of the sphincter. Tension in the MTCs generates laterocaudal traction on the perineal fascia; this pulls the sphincter away from the urethra causing a dysfunctional closure.
  Local varicose veins (anus, vagina, testicle) caused by perineal stenosis.
  Masculine Impotency. All men who suffer from impotency manifest tension in the MTCs. It is also associated with tension in the PTCs: resolution of tensions in both these TCs helps improve or resolve the problem.
  Alteration in the vaginal mucus may occur, presenting excess mucus or vaginal dryness (the latter causing dispareunia).
  Anorgasmia. The tension subjected by the MTCs to the local branches of the nerve may generate a deficiency in sensitivity.
  The tension in the MTCs submit the perineal fascia to tension. This, through transference, pulls on the retroprostatic and retropubic aponeuroses of the prostate. In such a case, this may compromise the haemodynamics. If this happens, prostate drainage through the venous and lymphatic system will become compromised; increasing hormonal stimulation time, which in turn facilitates benign prostate hypertrophy and the presentation of associated symptoms (post void dribbling and pollakiuria).

Compromised saphenous vein hiatus. A mild or severe stenosis of the hiatus of the saphenous vein may occur when there is tension in the MTCs. The most common symptoms depend on the seriousness of the stenosis; from slow and progressive liquid retention in the lower limb to the appearance of small or large varicose veins.

Lymphatic retention. The cribriform fascia has numerous foramina for the lymphatic ganglions and for the passage of the conducts. When tension arises in a MTC the lymphatic ganglions and ducts are compromised.

The femoral artery and vein run through the MTCs. Tension in the MTCs will, at times, compromise their correct functioning due to stenosis and is common to find symptoms of a circulatory origin: venous insufficiency, heavy legs, pain or discomfort of circulatory aetiology, or dysfunctional valves.

From Pelvis to Cervical Spine/Cranium

At the body portion ranging from the pelvis to the cranium both the LMTC and RMTC subdivide in a more external chain (the AATC) and a more internal one (the AVTC):

1. Anterior Abdominal Tensional Chain (AATC)
2. Anterior Vertebral Tensional Chain (AVTC)

Anterior Abdominal Tensional Chain (AATC)

The AATC continues via superficial fascia (scarpa and camper), rectus sheath, muscles and fascias of the abdominal external oblique and internal oblique, transverse abdominis, rectus abdominis, pyramidal, Cooper's ligament, and lacunar (gimbernat) ligament, median and medial umbilical ligaments. All of these are connected to the MTCs at the inguinal ligament and pubic symphysis.

The AATC ascends vertically in the space delineated by the anterior superior iliac spine and the linea alba, until it reaches the muscles and fascias pertaining to the AATC in the periosteum of the ribs, the xiphoid process, the sternum, the major pectoral fascia and the diaphragm. Also forming part of the AATC is the vascular, lymphatic, and nervous system and the peritoneum of the area covered by the AATCs.

The AATC continues through the pectoral fascia and its insertions into the sternum, manubrium, clavicle and humerus.

The pectoralis major muscle is rarely affected by tension in the AATC, as such, it is not considered a part of this tensional chain, but the pectoral fascia is. The pectoralis major muscle forms part of the transverse scapular chain (TSTC).

The AATC terminates in the anterior and middle scalenes, sternocleidomastoid, sternothyroid and sternohyiod. It terminates in this muscle group not because of a direct connective tissue relationship but because of the antagonistic effect that the AATC have on them. For example, when there is a tension present in the AATC (whether from tension in a MTC or not), the AATC exerts a caudal traction on the anterior thoracic cage. This creates a strain on or an overexertion of the anterior and superior inspiratory muscles of the thorax. The anterior and middle scalenes and also the sternocleidomastoid will become tense; this generates coaptation of the vertebral segment and will frequently be symptomatic. The tension on the scalenes and sternocleidomastoid, generate, on a postural level and in the majority of patients, an increased cervical lordosis and occipital extension.

When the ATC is tensioned at the perineum level the following may occur:

The most frequent cause of tension found in the AATC is tension in the MTCs. The AATC forms part of the MTCs, but when an MTC is tensioned this causes an anteversion of the iliac. This action is the contrary to that carried out by the AATCs; the latter acting as an antagonist (retroversion). To maintain this retroversion it uses the thoracic insertions of the myofascial system pertaining to the AATC as a fixed point, generating a chronic caudal thoracic tension. Within the same chain we find established antagonisms between agonists and antagonists.

Possible Consequences of the Above Tensions:

Limited caudal movement of correct bucket and pump handle rib movement. The thoracic cage shows severely limited rib elevation. This leads to overuse of the muscles involved in inspiration (thoracic diaphragm, intercostals, rib elevator muscles, scalenes, and sternocleidomastoid) and they may be symptomatic.

Generates a thoracic kyphotic posture, due to shortening of abdominal muscles.

Acute or chronic pain, dorsal or lumbar contracture due to antagonism. The tension in the AATC generates a constant tension of abdominal and thoracic flexion; the extensor muscles of the spine (antagonists) have to work to neutralize the AATC. If the tension in the AATC is not deactivated pain will appear in the extensor muscles of the vertebral column.

The increase of load on the scalenes and the sternocleidomastoid (anterior inspiratory muscles), which generates tension in the AATC, may produce a variety of symptoms: anterior and caudal displacement of the cervical vertebral bodies (influences of scalenes); increased cervical lordosis (influences of scalenes); increased occipital extension (influences of sternocleidomastoid); limited ipsilateral cervical rotation on the side of the dominant AATC; and an increase in cervical and occipital lordosis.

Increased cervical vertebrae coaptation and also increased coaptation of the occiput on the atlas (influences of scalenes and sternocleidomastoid).

Acute and chronic cervical pain, limited joint articulation movement.

Vertigo and migraine.

Tension in the AATC increases the anterior load in the lumbar and dorsal vertebrae which facilitates joint articulation degeneration and disco pathology.

It may produce a stenosis in venous return and lymphatic drainage causing slow and progressive fluid retention in the abdominal area.

Increased pressure on the abdominal viscera and organs, leading to diminished movement. For example, presenting symptoms may be urinary continence caused by increased abdominal pressure which causes greater pressure on the bladder and sphincter.

Having limited thoracic cage movement, the lungs and bronchioles receive fewer stimuli for movement; debilitating them and diminishing their efficiency. The increase in coaptation of cervical and thoracic vertebrae and the occipital-atlas complex contribute to the occurrence of stenosis in branches of the autonomic nervous system (the vagus nerve, or the cervical and/or thoracic sympathetic chain, or the efferent branches of the intercostal muscles or the diaphragm controlled by the phrenic nerve). This contributes to the debilitation of the respiratory system and symptoms of bronchitis, asthma or pneumonia may present.

Anterior Vertebral Tensional Chains (AVTCs)

The AVTCs are made up of the iliopsoas muscle and the iliac fascia, also all the blood vessels, nerves, lymphatic system, visceral system and the organs related to the iliac fascia and its expansions, and also the diaphragmatic fascia.

The AVTCs, psoas and iliac fascia are connected to the MTCs at the inguinal ligament, iliopubic eminence, and to connective tissue of the fascia lata descending from the sartorius and to that of the pectineus.

When there is tension in the MTCs in the lower limb there will be repercussions in the AVTCs.

When the AVTC is tensioned the following may occur:
Generates iliac anteversion (influence of the iliac), with increased lumbar lordosis (influences of the psoas).
Increases anterolateral coaptation of the lumbar vertebral bodies. Forces disc protrusion and disc pathology, conducive to formation of osteophytes in the anterior and lateral parts of the vertebral body.
The AVTC forces lumbar flexion. Consequently, there is an antagonism of the extensor muscles. These will act permanently as antagonists until the tensions in the AVTC and/or MTCs are deactivated.
Thickening or hypersensitivity of the inguinal ligament upon palpation. The iliac fascia merges with the inguinal ligament. The establishment of chronic tension in the AVTC generates greater and constant tension on the ligament which facilitates its thickening.
Stenosis in the branches of the lymphatic and vascular system, also in any part in contact with the connective muscle system that forms part of the AVTC.
Limited movement of the connective tissue related to the fascia lata (such as the kidney fascia, blood vessels, nerves, peritoneum, etc). It may provoke symptoms in the local viscera, vessels or organs.
Tension in the AVTC generates a postural lumbar flexion, and increased thoracic kyphosis.
The anteversion generated in the pelvis causes the AATC to act as an antagonist. The muscles and the abdominal connective system try to antagonize the movement and generate a retroverted Tensional Chain. This is why tension found in an AVTC is always accompanied by tension in the AATC, along with all the possible consequences and symptoms previously described.
It is a tensional chain that generates the intense feeling of physical and psychological fatigue in a patient. It generates a mood state of sadness with poor decision making ability.
It has a strong influence on the diaphragm and the respiratory system (blocking rib movement).

Lateral Tensional Chains (RLTC and LLTC)
From Foot to Knee

The LTCs run along the lateral side of the lower limb. They originate in the foot, in the tendons and connective elongations of the peroneus longus and brevis muscles. They are found in the lateral part of the fibular bone and are made up of the lateral compartment of the lower leg, the peroneus longus and brevis muscles and their respective fascias, the superficial peroneal nerve, one fifth of the external soleus and its fascia, the external part of the superficial posterior compartment and the superficial fascia (connective tissue of the dermis and hypodermis). The LTCs ascend the lateral part of the lower legs until they reach the fibular head where the peroneus longus muscle and the lateral compartment of the lower leg insert having expansions to the lateral condyle of the tibia, passing in front of the tibiofibular joint articulation. The lateral fibres of the soleus muscle insert into the lateral and posterior aspect of the fibular head. The lateral collateral ligament connects the fibular head to the lateral femoral condyle.

When the LTCs are tensioned at the foot level the following may occur:
It alters the biomechanics of the foot. The patient manifests pronation in dynamic movement. The LTCs are the cause of the pronation; they misrepresent the pronation and shoe insoles would be contraindicated.
Tension in the LTCs, via the tendinous insertions in the foot, generates direct coaptation on the first and fifth tarsometatarsal articular joints, this indirectly coapts the second tarsometatarsal joint.
The patient presents stiffness in the fifth tarsometatarsal articular joint: this is particularly observed when the patient puts all their weight on the affected foot. It may lead to a fracture of the fifth tarsometatarsal; especially in sportspeople.
There is a dominance of the fibular bone; creating dysfunctional movement.
Pain in tendons and synovial tissue.
Pain in local ligaments and periosteum.
When walking, forced dorsal flexion is shown to be limited and is associated with medial rotation of the tibia, the fibula and the knee complex (the patient loses the correct axis of knee flexion). This movement produced by the LTCs on the foot and the knee compromises the medial and anteromedial aspect of the knee.

From Knee to Pelvis

At femoral level, the LTCs continues along the iliotibial tract. They insert into the anterior and lateral tibial condyles, merges with the fibulae, and send out connective expansions along the lateral aspect of the knees; superficial fascia, lateral patellar retinaculum, the patella, the distal articular joint capsule. The LTCs ascend the iliotibial tract, merge with the tensor lata fascia, the connective tissue of the iliac crest, gluteus medius, gluteus minimus and the respective fascias of these muscles.

When the LTCs are tensioned at the knee level the following may occur:
Pain and inflammation of the proximal tibiofibular articular joint.
Pain in the tibialis anterior muscle, via the prolongations of the iliotibial tract on the tibial fascia.
Limited articular joint movement of the tibia with respect to the femur, both in medial and lateral rotation.
Lateral joint coaptation, increased joint degeneration, facilitated degenerative processes.
The lateral collateral ligament (influences of the fibula) deteriorates and is predisposed to thickening, having increased tone and diminished flexibility.
Lateral displacement of the patella.

When the LTCs are tensioned at the pelvis level the following may occur:
Ipsilateral tilt of the pelvis.
Ipsilateral and contralateral rotation depending on the dominance of either the posterior fibres of the gluteus medius or the tensor of the fasciae latae.
Coapts and limits coxofemoral movement and facilitates degenerative processes.
The tensed LTCs cause thickening of the gluteal aponeurosis. These patients present stringy connective tissue along the iliac crest. Treating the thickening present in the iliac crest is of vital importance to deactivate the tension in the LTCs. If it is not deactivated, treatment of the LTCs will not be effective and the tension will reinstate.

From Pelvis to Cervical Spine

The aponeurosis and the gluteus medius muscles insert into the iliac crests and the LTCs continue on through the muscles and fascias inserted in the iliac crests (external oblique muscle, internal oblique muscle, transversus abdominis, transversalis fascia, peritoneum, quadratus lumborum). From the iliac crests the LTCs extends along the lateral aspects of the abdomen, and the lumbar, thoracic and cervical area. They ascend through the gaps formed by the iliac crests, quadratus lumborum, and lateral aspect of the thorax (intercostal muscles and fascias, ribs, lateral thoracic fascia and muscle and fascia of the serratus anterior). The LTCs terminate in the posterior scalenes.

The superficial fascia, nerves, blood vessels and lymph ducts form part of the LTCs and also those viscera and organs that contact the LTCs.

When the LTCs are tensioned the following may occur:
The LTCs produce ipsilateral thoracic flexion.
Increased lumbar lateral flexion (scoliosis)
Descended twelfth rib (influences of quadratus lumborum)
The interconnection of the renal fascia with that of the quadratus lumborum may cause poor renal function leading to; kidney stones, sand and kidney infection.
Tension in the quadratus lumborum generates a state of fatigue, physical or psychological astenia, general mood of sadness or at least emotional stress.
Tension in the right LTC causes a state of emotional frustration and heightened sensibility which lead to moods of anger or fury.
Ipsilateral vertebral coaptation.
Generated antagonism of the contralateral LTC.
Tension in the LTCs generates caudal tension on the lateral and posterior region of the thorax, especially via the external and internal oblique muscles, transversus abdominis and quadratus lumborum. This causes an overexertion of the lateral thoracic inspiratory muscle group, which may be symptomatic. It is the posterior scalene that most manifests symptomology (the anterior and middle scalenes belong to the anterior abdominal chain)
As we saw earlier the LTCs block movement in the ribs and thorax. This leads to decreased stimulation to the lung, pleura and bronchioles, also to blood vessels and nerves in the area. This blockage of movement may be conducive to respiratory symptoms (such as mucous production or mucous and bronchial irritation) and worsen illnesses (such as bronchitis, asthma or pneumonia).
Acute and chronic cervicalgia (influences of the posterior scalene)
Intercostal pain.
Respiratory difficulty.

Anterior Tensional Chains (RATC and LATC)

They cross the lateral aspects of the lower legs.

From Foot to Knee

They begin in the tendinous and fascial insertions of the extensor muscles of the feet and of the anterior compartment of the lower legs (comprising the tibialis anterior, extensor hallucis longus, extensor digitorium longus, peroneus tertius, anterior tibial vein and artery and the deep peroneal nerve). The anterior compartment runs along the space created between the anterior aspect of the tibia and fibula; the aponeurosis merges with the periosteum of the tibia and fibula; and the anterior crural intermuscular septum separates the ATCs from the LTCs. The muscles which form part of the ATCs insert into the tibial and fibular bones.

At the proximal end of the lower legs, the ATCs insert into the anterior and lateral aspects of the tibial plateaus. On an aponeurotic level they merge with patella tendons, the patellae, and the anterior and lateral aspect of the articular joint capsules. The ATCs have a direct relationship with the iliotibial bands (influence of LTCs), the lateral patellar retinaculums, the tendons of the biceps femoris muscle (influences of PTCs), the periosteum and fasciae of the peroneal muscles (influence of LTCs). Tension in the ATCs is often the cause of a chronic problem in the LTCs.

When the ATCs are tensioned at the foot level the following may occur:
Favours pronation in dynamic movement, with pes planus, and favours medial rotation of the tibia and knee. This dysfunctional movement arises when the antagonism of the anterior chain is not efficient, especially in the lateral and posterior chains. The antagonisms of internal tibial and fibular rotation are not stable.
Coapts and limits the tibiotalar articular joint.
Anterior, medial and caudal traction on the fibula (influence of the LTCs), especially by the musculofascial components of the tibialis anterior and the extensor digitorium longus.
Coaptation generated in all articular foot joints.
Limited flexion movement.
When plantar flexion is tested on the supine lying patient flexion in the knee occurs; associated with a medial rotation of the whole of the lower limb.
The ATCs join the iliotibial bands via the tibialis anterior and its fascia. The ATCs have a strong influence on the LTCs. Tension in the ATCs often being the primary cause of a symptomatic/asymptomatic LTCs.
Possible dysfunction of tibioperoneal ligaments.

From the Knee to the Pelvis

The ATCs ascend from the patellar tendons, the patellae and the anterior articular joint capsules up through the anterior compartments coming from the fascia latae, and from the quadriceps (vastus lateral, vastus intermedius, vastus medial, and rectus femoris).

When the ATCs are tensioned at the knee level the following may occur:
Dysfunction or pathological patellar processes.
Patellar tendinitis.
Coaptation and limited articular joint movement.
Traction on the fibular collateral ligament, which may be the cause of chronic pain in said region.
The ATCs merge with the LTCs and may provoke many painful symptoms both at knee level and at pelvic level.

From Pelvis to Cervical Spine/Cranium

The ATCs have little influence on structures above the pelvis, principally because there are few insertions in the iliac bones. These do not have leverage as the main insertions are found in the femur and these do not have the strength to modify pelvic parameters.

However, when the ATCs show a history of fibrillar rupture, then it has an importance on pelvic structure. The process of fibre reconstruction subsequent to fibre rupture may set off a retractile process in the ATCs and exert greater force on the iliac; facilitating anteversion. If this happens, the tension continues along through the AATCs, and will perhaps show any of the symptoms associated with tension in this Tensional Chain.

Posterior Tensional Chain (RPTC and LPTC)

They cover the posterior aspect of the lower leg.

From Foot to Knee

They originate in the plantar aspect of the feet, in the tendinous and fascial insertions of the flexor digitorum brevis, abductor hallucis, abductor digiti minimi, flexor hallucis brevis and digiti brevi, lumbricales, quadratus plantae, the plantar ligaments, the plantar aponeurosis, the lateral band of the aponeurosis plantar, and the oblique head of the adductor hallucis.

The PTCs continue along the calcaneal tendons, the muscles and fascias of gastrocnemius (the medial fibres of the medial gastrocnemius correspond to the CTI) and the soleus (except for one fifth of the medial and lateral fibres which correspond to the MTC and the LTC respectively); via the deep posterior compartment of the lower leg (except for one fifth of the medial and lateral fibres which corresponds to the MTC and the LTCs), and via the popliteus muscle and plantaris muscle. The fascial extensions of the gastrocnemius, soleus and popliteus muscles merge with the posterior periosteum of the femoral condyle, tibial plateau and the posterior articular joint capsule of the knee.

The superficial fascia makes up part of the PTCs, as do the neural, lymphatic and vascular systems extending through the area of the aforementioned compartments and muscles. Of note; the minor saphenous vein, the posterior tibial arteries and veins, the tibial nerve, the calcaneus, the plantaris and sural muscles, also the posterior and terminal branches of the saphenous nerve.

Interconnections of the PTCs:
The central fibres of the soleus join the MTCs via its medial fibres; on the external aspect, the medial fibres join the LTCs via the lateral fibres of the soleus.
When the tibial nerves perforates the soleal hiatus and enters the deep posterior compartment they join the MTCs.

When the PTCs are tensioned at the feet level the following may occur:
Plantar fasciitis.
Calcaneal spurs.
Achilles tendinitis.
Dorsal flexion limitation.

From Knee to Pelvis

The fascias of the medial gastrocnemius connect with the semimembranosus and semitendinosus muscle in the popliteal region; the lateral gastrocnemius merges with the biceps femoris. The PTCs ascend through the fascial system and superficial compartments of the hamstrings up to the pelvis. This muscle unit and its fascia insert into the ischium. The posterior portion of the hamstrings fascia merges with the gluteus maximus fascia (anterior portion and the end of the inferoposterior portion). The superficial fascia of the hamstrings merges directly with the superficial fascia of the gluteus maximus.

At the pelvis, the PTCs continue along the gluteus maximus and the underlying muscles (piriformis, pirimidalis, gemellus superior and inferior, obturatus externus and internus, quadratus femoris). The PTCs reach the posterior iliac spine and also the anterior and posterior sacrum via the piriformis and the gluteus maximus (it joins the LTCs via its insertion in the iliotibial bands). The pelvic muscles of the PTCs join the greater trochanter and the femur.

The PTCs is of great importance in the posterior pelvis on a neurodynamic level, of particular importance; the sciatic nerve, the pudendal nerve, the posterior femoral cutaneous nerve and the superior and inferior gluteal nerves. The sciatic nerves are dependent on the PTCs up to the popliteus muscles: here, the peroneal nerves, once above the head of the fibulae, will be dependent on the LTCs. The tibial branches are dependent on the PTCs until they pass the soleal hiatus. When the tibial nerves enter the deep posterior compartment they are dependent on the MTCs.

The PTCs are of great importance on a lymphatic level in the popliteal fossae, where the popliteal lymphatic nodules are found. These are dependent on the PTCs.

The posterior pelvic diaphragm forms part of the PTCs, thanks to the interconnections of the connective system of the hamstrings in the ischial tuberosity and the gluteus maximus in its insertion in the sacrococcygeal symphysis. The two extensions communicate through the connective tissue system with the muscles of the posterior pelvic diaphragm (levator ani, ischiococcygeus and obturator internus muscles) and the anococcygeal ligament. PTCs control of the pudendal nerves makes these TCs ones of the most important in the pelvic diaphragm and for proper functioning of the perineum.

Interconnections of the PTCs:
Merges with the LTCs when inserting the iliotibial bands via the gluteus maximus muscles.
Merges with the MTCs in the pes anserinus via the semitendinosus muscles.
Merges with the LTCs at the fibular heads via the biceps femoris muscles.
Merges with the vertebral PTCs (VPTC) via the gluteus maximus and the piriformis muscles.

When the PTCs are tensioned at the knee level the following may occur:
Stenosis in the lesser saphenous veins.
Stenosis in the popliteal lymphatic nodules.
Delays post operative recovery time in the knees; particularly oedema and haematoma. The PTCs control a large part of knee drainage.
Increase in the degenerative articular joint processes of the knees; both the gastrocnemius and the hamstrings are posterior joint coaptors. Their tendofascial insertions merge with the periosteum and the articular joint capsules: the tension created in these structures causes stenosis in the vascular system. It increases joint coaptation, with limited rotation of the tibial plateau with respect to the femur.
It may initiate compression on the neural and vascular systems in the region, generating symptoms specific to compression of these nerves and veins (tibial nerve, cutaneous sural nerve, peroneal nerve or lesser saphenous vein and posterior tibial veins).

When the PTCs are tensioned at the pelvis level the following may occur:
Iliac and sacral retroversion (contranutation).
Contralateral pelvic rotation.
Homolateral lateral flexion (sidebending).
Stenosis of the sciatic, pudendal, posterior cutaneous femoral, superior and inferior gluteal nerves.
Changes in tension in the posterior pelvic diaphragm. This is often associated with pudendal stenosis, causing dysfunctions in sphincter, urethra, anus, blood vessels, and pelvic viscera (ovaries, prostate, bladder, fallopian tubes, uterus . . . ) functioning. Hence, the following problems may appear: urinary and faecal incontinence, uterine myoma, endometriosis, altered lubrication and sensitivity in the vagina, altered vasculature, benign prostate hypertrophy, post void dribbling, impotence, anorgasmia etc.
Dysfunction of the sacral autonomic nervous system (ANS). Both the gluteus maximus and the piriformis muscles insert into the sacrum; one in the anterior aspect and the other in the posterior aspect. Both can create tension on the ANS leading out of the sacrum, altering biofeedback and causing symptoms related to abnormally stimulated nerves, i.e., as occurs with an over stimulated bladder. Tension in the PTCs may generate all types of dysfunction (in viscera, blood vessels and lymphatic ducts, glands or sphincters) in the pelvic system.

From Pelvis to Cervical Spine and Cranium

They are made up of the following muscles and their fascias:

Longissimus, iliocostalis, spinalis.

Posterior and middle thoracolumbar fascia (not the anterior lamina, which belongs to the LTC).

Multifidus, levatores costarum, rotatores spinae longus and brevis, interspinales, intertransversarii.

Connective tissue (fascias, ligaments, tendons) which insert in the sacral spinal apophyses, lumbar, dorsal and cervical vertebrae, and terminates in the external occiput protuberance (nuchal ligament, supraspinal and infraspinal ligaments)

Posterosuperior and inferior serratus.

Trapezius and rhomboids.

Splenius capitus and cervicus, longissimus capitus.

Semispinalis capitus, rectus capitus posterior major and minor, inferior and superior obliquus capitus.

The PTCs enter the pelvis where they insert in the ischium, posterior aspect of the sacrum, coccyx, iliac crests and posterior iliac spines via the muscles and fascias of the hamstrings and gluteus maximus. The gluteal fascial system joins the connective tissue of the iliocostalis, longissimus and spinalis muscles and the thoracolumbar fascia, connecting with it to give continuity to the posterior tensional chain. It extends through the topography of the muscles and fascias pertaining to the PTCs.

The PTCs terminate in the superior and inferior nuchal lines, posterior aspect of the mastoids, via insertions from the trapezius, splenius capitus, longissimus capitus muscles and suboccipital muscles.

On a neurological and vascular level the dorsal nerve branches and spinal blood vessels make up part of the PTCs.

When the PTCs are tensioned at the vertebral level the following may occur:

When there is tension present in a PTC, at lower limb level, the hamstrings and gluteus maximus generate retroversion of the iliac and of the sacrum (contranutation) with an increased posterior stretch on the lumbar vertebrae. The multifidi muscles and erector muscles of the spine act as antagonists. Hence, when there is tension in a PTC in the lower limb this leads to tension in the PTC at lumbar level. This is due, initially to the relationship with the fascial system and then, due to the biomechanical antagonism it has with respect to the movements of the iliac, sacrum and lumbar vertebrae. The PTC generates chronic lumbago.

Fascial or muscular pain, in any part of the PTCs vertebral area. For example; lumbalgia, dorsalgia or cervicalgia.

Vertebral articular joint pain. The erector muscles of the spine are posterior vertebral coaptors. Increased tone generates tension and/or posterior vertebral coaptation on the spinal and transverse apophyses, joint faces and invertebral disc, and limits vertebral rotation and flexion.

Neuropathic pain. Tension in the PTCs at vertebral level (VPTCs) can generate neuropathic pain in two ways:

Muscular and fascial tension may compress the dorsal branch.

Increased joint coaptation may diminish or compress the invertebral foramen and compress the perineural or dural sheath.

Descended glenohumeral joint articulations. This problem appears when there is a dominance of the inferior trapezius fibres and the latissimus dorsi muscle in the VPTCs.

It can increase lordosis at lumbar and cervical levels.

Costovertebral pain. Principally initiated by the iliocostalis muscles (caudal coaptors).

Tension in the iliocostalis muscle induces limited inspiration due to caudal traction on the ribs; this generates overuse of the posterior inspiratory muscles (superior posterior serratus, intercostals and levatores costarum).

The erectors of the spine terminate in the cervical vertebrae, the trapezius and the semispinalis muscles at the nuchal line, and generate cervicalgia associated with limited articular joint movements Migraine, due to tension in the trapezius and suboccipital muscles, which cause stenosis, principally, in the greater occipital nerve.

Tension in the VPTCs generates limited vertebral flexion and generates flexion in group block with a loss of posterior stretch.

Transverse Scapular Tensional Chain (TSTC)

This chain is made up of the muscle and fascias which are involved in shoulder abduction and adduction, whether or not they insert into the scapula itself.

It is a TC which strives against the scapular adductors and abductors to maintain its position. For example, when there is tension in a scapular muscle abductor, the muscles involved in the opposite action (adduction) enter in an antagonism to maintain the position of the scapula.

Muscles of the TSTC which participate in scapular abduction:

Anterior deltoid.

Pectoralis major.

Serratus anterior.

Muscles of the ECTC which participate in scapular adduction:

Trapezius (middle fibres).

Rhomboids.

Levatator scapulae.

If we want to definitively resolve a specific tension in any muscle in this chain we have to analyse its antagonist to find out whether it is affected or not.

The topographies of all the previously mentioned Tensional Chains include as integral parts of the Tensional Chain; the dermis, hypodermis, nerves, blood vessels, lymph ducts, glands, tendons, fascias, periosteum-tendon unions, periosteum fascias and the periostio-aponeuroses of the muscles mentioned or any other structure present in the human body in the region of where the Tensional Chain passes.

As mentioned earlier, all the tension in a Tensional Chain stems from a primary lesion which is often non-symptomatic. The identification of the myofascial chain involved, its assessment, the identification of the primary lesion (point of origin) and the treatment of at least the primary lesion will be key to a successful symptomatic treatment.

Thus, one step in the SD method is to identify with precision the state of tension or health of the myofascial and joint units constituting the tensional chain to which the lesion or condition associated with the symptoms reported by the patient belongs.

The Saló-Darder evaluation method (SD method) involves the following steps:

Exploration of the state of the muscle and fascia (hereinafter, myofascial unit) and the effect the myofascial unit has on the joint, and Evaluation using a rating scale of the following features:
- the state of tension or health of the myofascial unit itself
- the existence of tension exerted on the joint by the myofascial unit or units (dominating the joint), i.e., whether the joint is subject to tension, joint coaptation, vascular stenosis or stenosis of the periarticular nerve caused by the retractile process of the myofascial unit or units that are inserted into the joint.

To undertake the above-mentioned evaluation a 4-step approach is followed:
1. the patient is placed in the correct position to permit the evaluation to be made.
2. the anatomical location of the evaluation point(s) to be examined in the myofascial unit is/are located as described below and the fingers are positioned at the evaluation point(s).
3. the direction of movement of the evaluation points is determined and it is compared with the normal direction of movement for the corresponding myofascial unit in healthy conditions.
4. the degree of tension and mobility of at the myofascial unit or joint being evaluated is determined.

We will now look at each of these elements in greater detail:

Step 1. Placing the Patient in the Correct Position for Making the Evaluation.

The position in which the patient must be placed to make the evaluation is of primary importance. Each myofascial unit or joint to be evaluated requires the patient to be in the correct position for the myofascial unit to be examined to be stretched. There are three types of position: standing, sitting or prone.

If the patient is not in the correct position the evaluation may not be effective. The section entitled "Position of the patient and stretching maneuver based on the evaluation point" describes the correct anatomical position of the patient, depending on the myofascial unit and joint which are to be evaluated.

Step 2. Anatomical Location of the Evaluation Point in the Myofascial System and Positioning of the Fingers on the Evaluation Point.

The SD method has created the "evaluation point" that is required to make the evaluation. Consequently:
- each myofascial unit has its own evaluation point which is located in a precise and specific site in the myofascial unit.
- the evaluation points of each joint coincide with the evaluation points of each myofascial unit that dominates the joint.

The SD method has designed a body map on which all the myofascial and joint evaluation points are indicated.

After locating the evaluation point, the practitioner touches the myofascial unit to be evaluated with his hand, keeping his fingers on the evaluation point at a precise angle (which depends on each evaluation point). This way, he can evaluate the movement of the evaluation point when the patient stretches the fascia, as described in the next phase.

Step 3. Observing the Direction in which the Evaluation Points Move.

Once the patient is in the correct position (sitting, prone, standing) and the practitioner has established digital contact with the evaluation point, the patient is asked to make a movement, in order to stretch the myofascial unit that is being evaluated and observe whether the movement of the evaluation point (i.e., the fascia) is correct or limited when the myofascial unit is stretched.

Step 4. Determining the Severity of the Lesions at the Myofascial Unit or Joint being Evaluated.

To evaluate the severity of a lesion the following aspects need to be assessed: a) the muscular tension, b) the myofascial mobility and c) the mobility of the superficial fascias with respect to the myofascial unit evaluation. The different aspects are explained in detail below:

a) Muscular Tension Assessment.

The practitioner palpates the myofascial unit and compares the myofascial tension with its counterpart on the other side of the body. The degree of myofascial tension (MT) is assigned according to the following 4-grade scale: Grade 3: Severe muscular tension with inflammation and pain on palpation; Grade 2: Significant muscular tension with no inflammation and no pain on palpation; Grade 1: Moderate to mild muscular tension with no inflammation and no pain on palpation; and Grade 0: Same tone as its healthy counterpart on the other side of the body: the myofascial unit is pliable.

b) Myofascial Mobility Assessment.

The practitioner stretches the myofascial unit to evaluate its range of mobility, elasticity and/or range of movement of the dominant articulation. The degree of myofascial mobility is assigned according to the following 4-grade scale: Grade 3: the myofascial unit presents severe stretch limitation or shows an incorrect movement upon being subjected to a small tension, Grade 2: the myofascial unit presents significant stretch limitation or shows an incorrect movement upon being subjected to an intermediate degree of tension, Grade 1: the myofascial unit presents moderate stretch limitation or shows an incorrect movement upon being subjected to full tension, Grade 0: no observable stretch limitation.

c) Mobility of Superficial Fascias with Respect to the Myofascial Unit Assessment.

The assessment is conveniently made using the device described in international patent application WO 2011/101388 A1, or other devices capable of applying vacuum/pressure or to achieve similar results with other means. The vacuum devices (including the one described in WO 2011/101388 A1) allow the application of suction to the area being assessed. To effect the assessment the practitioner places the applicator (110) on the area to be assessed. Then suction is connected and while the suction forces grips the hypodermic fascias the practitioner tries to move the applicator in 8 directions parallel to the skin plane (north, northeast, east, southeast, south, southwest, west and northwest). When adhesions between the superficial fascias and the underlying myofascial unit exist the practitioner is capable of sensing a resistance to the movement in one or more of the 8 directions which indicates the presence of adhesion between the different fascial planes. Conversely, when no resistance to movement is sensed and the fascias move correctly, this indicates that there are no adhesions between the planes (superficial fascia and myofascial unit).

Stretching Maneuver and Patient's Position, Depending on the Evaluation Point

As described above, each evaluation point requires the performance of a specific type of stretching maneuver to determine the extent of the state of tension or health of the myofascial unit. The stretching movements are detailed below for the different evaluation points:

1. Hip Flexion (Standing):
   a) EP (evaluation point) fascia and muscles in the posterior region of the thoracic, lumbar and sacral sections of the spine.
   b) EP fascia and muscles in the posterior hip region.

c) EP fascia and muscles in the lateral and posterior hip region.
d) EP fascia and muscles in the posterior femoral region.
e) EP fascia in the posterior knee region.

2. Hip Extension (Standing):
a) EP fascia and muscles in the anterior abdominal region.
b) EP fascia and muscles in the anterior hip region.
c) EP fascia and muscles in the lateral and anterior hip region.
d) EP fascia and muscles in the medial femoral region.
e) EP fascia and muscles in the anterior femoral region.
f) EP fascia and muscles in the lateral femoral region.

3. Stretching of Abdomen (Prone), with Maximum Inspiration:
a) EP fascia and muscles in the anterior abdominal region.
b) EP fascia and muscles in the diaphragm region.
c) EP fascia and muscles in the inferior thoracic region.

4. Stretching of Thorax (Prone), with Maximum Thoracic Inspiration:
a) EP fascia and muscles in the thoracic region.

5. Knee Flexion (Prone):
a) EP fascia and muscles in the anterior femoral region.
b) EP fascia and muscles in the knee.
c) EP fascia and muscles in the patella.
d) EP fascia and muscles in the tibial plateau region.

6. Foot Flexion (Standing).
a) EP fascia and muscles in the anterior leg region.
b) EP fascia and muscles in the lateral leg region.
c) EP fascia and muscles in the posterior leg region.
d) EP fascia and muscles in the medial leg region.
e) EP fascia and muscles in the posterior knee region.

7. Lumbar Glexion (Standing).
a) EP fascia and muscles in the lateral and posterior trunk region.
b) EP fascia and muscles in the lateral trunk region.
c) EP fascia and muscles in the lateral and anterior trunk region.
d) EP fascia and muscles in the lateral thoracic region.

8. Cervical Flexion (Standing, Prone or Sitting).
a) EP fascia and muscles in the lateral cervical region.
b) EP fascia and muscles in the muscles of the upper thoracic region and upper scapular region.

9. Cervical Flexion (Standing, Prone or Sitting).
a) EP fascia and muscles in the posterior cervical region.

10. Cervical Extension (Standing, Prone or Sitting).
a) EP fascia and muscles in the anterior cervical region.

11. External Rotation and Abduction of the Glenohumeral Joint (Prone, Sitting, Standing).
a) EP fascia and muscles in the anterior thoracic region.

12. Flexion of the Glenohumeral Joint (Prone, Sitting, Standing).
a) EP fascia and muscles in the posterior glenohumeral region.
b) EP fascia and muscles in the scapular region.

We will now take a look at the types of treatment that can be applied to injury chain lesions.

Detailed Explanation of the Method of Treatment

Treatment of the lesions intervening in the injury chain is performed by carrying out one or more of the following correcting actions, depending on the type of lesion:
1. Decontraction of muscles and fascia.
2. Relieving tension in the muscle and fascial fibres.
3. Relaxing the sarcomerus.
4. Stretching and moving the different muscle and fascial planes.
5. Recovery of joint movement parameters.

In the context of the present invention a lesion is identified as an alteration of a myofascial unit whereby said myofascial unit presents one or more of the following characteristics a) abnormal muscular tension, b) limitation of the myofascial mobility and c) limitation of the mobility of the superficial fascias According to one aspect of the present invention the treatment of each lesion is advantageously effected using mechanical devices for the application of localized vacuum/pressure stimulus of variable intensity, such as a series of vacuum pulses, to the body areas to be treated. In particular, the use of the device described in international patent application WO 2011/101388 A1, which is hereby incorporated by reference in its entirety, has proved to be specially convenient and effective for treating the lesions (such as, for example the primary lesions) and this constitutes an embodiment of the present invention. This device comprises a suction machine having suction means for applying vacuum to a patient (e.g. according to several possible vacuum patterns) through at least one applicator (110). Advantageously, this device makes possible treating patients by sanitary and cosmetic professional personnel at any position on a stretcher, in a wheelchair or even standing up and in general in situations where he/she has to be treated by said device.

The device has several suction cups or applicators (110) connected to their respective hoses which are in turn connected to a device capable of generating negative pressure. In this way the suction cup facilitate the application of vacuum to any selected portion of the patient's body. In addition, the practitioner when bringing the suction cup in contact to any given portion of the patient's body may also exert force on the suction cup thereby creating a positive pressure in the areas where the walls of the suction cup get into contact with the patient body. In this way it is possible to combine positive pressure (exerted by the walls of the suction cup) with negative pressure (vacuum applied through the cup-hose system).

In a particularly advantageous embodiment of the present invention the treatment of the lesions may be carried out by applying to the area to be treated a pulsating vacuum stimulus for a period ranging from 1 minute to 3 hours, for example using a suitable device such as the one described in WO 2011/101388 A1.

The vacuum stimulus that will help massaging and moving different tissue planes at the treated zone is a stimulus of variable intensity such as a series of vacuum pulses. The vacuum is created through negative pressure and is applied to the area in need of treatment in the form of a pulsating pattern through one or more applicators. The pulsating pattern comprises a series of pulses regularly spaced apart in time wherein a maximum vacuum force (MAXIMUM VACUUM) is applied to the area being treated for a first predetermined time period (PULSE LENGTH). The maximum vacuum force is reached progressively along a second time period called TIME UP After the maximum vacuum force is reached it is maintained during a PULSE LENGTH and then the vacuum is decreased to a second value (MINIMUM VACUUM) during a third time period (TIME DOWN). The MINIMUM VACUUM is then maintained for a fourth time period (RELAXATION TIME). Afterwards a new pulse begins and several pulses are applied forming a treatment wave with a total duration designated as total wave time. This pulsating vacuum pattern is illustrated in FIGS. 13 and 14. In one particular embodiment it is also possible that the MINIMUM VACUUM takes a negative vacuum value i.e. that during the RELAXATION TIME a positive pressure is applied. The vacuum stimuli are conveniently applied through suction cups or applicators (110) which, upon application onto the patient's skin in the area to be treated, cover a certain area of the skin (i.e. the area encompassed within the perimeter defined by the applicator's perimetral rim). Depending on the size of the area to be treated applicators of different sizes may be used. In one embodiment of the invention the applicators may define areas of 17 $cm^2$, 42 $cm^2$ and 72 $cm^2$. The size of the applicator used for a given treatment will depend on the extension of the area to be treated. As a general rule the larger applicator is selected that can be applied to the area to be treated in such a way that the applicator's perimetral rim is fully contacted with the patient skin so that no air is allowed to enter the applicator when vacuum is turned on. As an exception to the former rule when a treatment is to be applied to a scar the smaller applicator is used first, The sloped trapezoidal profile of the individual pulses applied has been shown to be particularly advantageous since the progressive vacuum increase from the MINIMUM VACUUM value to the MAXIMUM VACUUM value and the progressive decrease from the MAXIMUM VACUUM value to the MINIMUM VACUUM value allows to apply the vacuum treatment in such a way that the sensation of discomfort experienced by the patient is minimized. This may allow for the application of more intense vacuum and/or the application of vacuum for longer time periods resulting in an enhanced treatment.

The application of suction (vacuum) with the help of the applicator (110) results in the movement and stretching of the tissue wherein the central portion of the tissue zone where the applicator is applied will be subjected to the highest stretch in the direction of the vacuum while the points where the perimeter of the applicator (110) contacts the zone where it is applied will either not be stretched in the direction of the vacuum (when the applicator is simple contacted to the patient skin without applying any pressure) or will be stretched in an opposite direction (if the applicator is applied to the skin exerting a certain force). This is illustrated in FIG. 15:

1. THE POINT OF GREATEST MOBILIZATION (or maximum stretch in the direction of the vacuum is located at the center of the applicator. This is the area where the greatest movement of tissue planes, greatest tissue stretch and greatest tissue massage of tissue layers is produced via the force of suction of the vacuum created.

2. THE FULCRUM POINTS are located in at the perimeter of the applicator contacting the skin. The tissue in contact with the perimeter of the applicator receives a positive force towards the skin.

The result is a stretch tension produced due to the force of negative suction. The cutaneous tissue and superficial fascias nearest to the FULCRUM POINT are those that most relax.

The application of vacuum to the zones to be treated as explained above results in one or more of the following benefits:

Summarizing a correct combination of the 6 control parameters as explained in detail below for different type of treatments permits the configuration of a large number of massage effects (generally with the fixed arms of the terminal) as well as specific work for the mobilization of localized tissue (generally with the mobile arms, but also with the fixed arms). All these parameters are adjustable at all times by the practitioner without needing to stop the massage being applied by the apparatus.

These massage effects can be applied on:
The muscular and Fascial system
The articular system
The connective tissue system
The venous system
The lymphatic system
Microcirculation
Fibrosis/adhesions Treatment of the Muscular and Fascial System:
1. Decontraction of muscles and fascia.
2. Relaxation of tension in muscle and collagen fibres.
3. Relaxation of the sarcomere.
4. Increase in the pliability of the connective and muscular system.
5. Massage, stretch and mobilize the different muscular and fascial planes.
6. Drainage of toxic metabolites.
7. Increase muscle recovery after physical exertion.
8. Achievement of local anti-inflammatory effects.
9. Increase of tissue regeneration after fibre rupture.

In a further aspect of the invention, once the tensional chain affected and the primary lesion have been identified, the practitioner will proceed to treat the primary lesion. After treating the primary lesion the practitioner should re-evaluate the entire injury chain and, in the event that symptoms persist at any point of the tensional chain, the practitioner must identify the new primary lesion (a different one from the first lesion which has already been treated and normalised) and will eventually treat it. This process may be repeated as many times as necessary. Nevertheless, in order to avoid the need of repeated re-evaluations after every single treatment step, the practitioner may alternatively decide to treat the complete injury chain starting from the primary lesion (the lesion in the most caudal position in the injury chain) and continuing with the treatment of the rest of the myofascial units in the injury chain in the foot to head direction.

The precise nature of the treatment applied according to the present invention will depend on the assessment of a) the muscular tension, b) the myofascial mobility and c) the mobility of the superficial fascias with respect to the myofascial unit evaluation as explained above.

When both myofascial mobility and muscular tension have been assigned to Grade 0 the myofascial unit is considered to require no treatment.

If either myofascial mobility or muscular tension assessments have been assigned to Grade 2 or Grade 3 a two-phase treatment is indicated as described below:

Phase 1 (Relaxed Position/Stretch Treatment):
The aim of this phase is to reduce muscular tension, increase range of mobility to a Grade 1 value. After achieving this goal, phase 2 is carried out.

In Phase 1 the practitioner operating the device described in WO 2011/101388 A1 positions one or more applicators (using a fixed or mobile arm depending on which myofascial unit is being treated) upon the myofascial unit to be treated, in order to apply the treatment dosage. At the same time, using the other hand, the practitioner repositions the myofascial unit being treated using relaxed position and stretch movements. The entire area of the myofascial unit has to be treated with the applicator while the practitioner performs the relaxed position-stretch movements using his hands or an electric treatment bed. To distribute the treatment dosage evenly to all points of the muscular and fascial group being treated, the treatment dosage is applied in several steps as described below:

First, the heads are placed covering all the origins and insertions of the whole muscular and fascial group being treated and then a first treatment step is applied. The duration of each treatment step varies between 1 min and 120 min depending on the program selected.

Once the first application step is finalized, the applicator's heads are displaced (between 0.5 cm and 15 cm depending on the muscle and type of treatment) to cover a new untreated area of the myofascial unit and a new treatment step identical to the previous one is performed. This process is repeated by shifting the applicators after each treatment step until the whole area of the muscular and fascial group has received the vacuum treatment. This is illustrated in FIG. 30.

The myofascial unit will progressively relax due to the effects of the applied massage, the limitation of mobility will diminish and the range of mobility will increase.

After Phase 1 treatment has been applied a second phase (Phase 2) is carried out. In Phase 2 a localized treatment is performed to treat painful points, adhesions, adhesion in planes, tension, retractile processes, spasticity, oedema and haematoma local to the muscular and/or fascial group, which may still persist after the first stage (Phase 1) of treatment.

If either myofascial mobility and muscular tension assessments have been assigned to Grade 1 a treatment comprising only Phase 2 (described above) is carried out.

In an embodiment of the present invention when performing treatment phases 1 and/or 2 described above the device described in WO 2011/101388 A1 is configured so that it exerts a pulsed suction through its applicators (110). It is particularly convenient to set the pattern of vacuum pulses applied with the device as follows:

The TIME UP will be fixed at a value comprised between 0.01 and 3 seconds; PULSE LENGTH will be fixed at a value comprised between 0.01 and 15 seconds, the TIME DOWN will be fixed at a value comprised between 0.01 and 2 seconds; and the MAXIMUM VACUUM value will be selected at a value comprised between 20 and 200 mbars taking into consideration the sensitivity of the area to be treated and the patient's tolerance; and the MINIMUM VACUUM value will be fixed at a value (in mbars) within the range of 0% to 30% of the MAXIMUM VACUUM value. The total length of pulse (TIME UP+PULSE LENGTH+TIME DOWN) is normally ranging between 0.03 and 20 seconds. The precise value will be established taking into consideration a number of factors such as the age and the physical constitution of the patient, and the tissue sensitivity of the area to be treated.

When, as a result of the diagnostic, the practitioner has treated with vacuum one or more affected myofascial units in one side of the body it is possible that an unbalance is originated in the biomechanics of the pelvis, knee, vertebral column, craneo-cervical area, and/or scapular area. In effect, the efficiency of the treatment in reducing tension and making the pathological myofascial unit more pliable at the side of the body that, has been treated may result in that this side ends up having more mobility than its counterpart on the other side (which was initially the more healthy), leading to problems of biomechanical adaptation at pelvic and vertebral level. For this reason, it is advisable to repeat the treatment on the other side of the body so that both sides are equally treated thereby facilitating the biomechanical adaptation. Nevertheless, it is not necessary to treat the myofascial units at the contralateral side of the body with the same intensity applied to the side of the body having the lesion. Consequently ratio between the number of vacuum treatment dosages applied to the affected myofascial unit(s) and the number of vacuum treatment dosages applied to the counterpart myofascial unit (the healthy one) is higher than 1:1, preferably between 1:2 to 1:10, more preferably between 1:10 and 1:100.

Treatment of Articulations

In the case that the myofascial unit treated is an articulation the following benefits may be obtained from the treatment:

1. Restoring range of joint motion.
2. Alleviating joint pain of any kind.
3. Ameliorating degenerative joint disease.
4. Draining intraarticular and periarticular oedema.
5. Decreasing articular coaptation.
6. Ameliorating spasticity or retractile process on a joint Before starting the treatment of an articulation or joint it is advisable for the practitioner to analyze the degree of flexibility or restriction of the myofascial units that insert into that joint and rate them using the rating system explained in the "Fascial and muscular system" section. If a myofascial restriction is found, it is necessary to first treat the myofascial unit or units which have insertions in the affected articulation because limited joint movement may be due to tension present in the myofascial unit- or myofascial units—which insert into the joint. In effect, the points of origin and insertion of the myofascial unit (via osteotendinous unions) are found in the periarticular area, where they exert different motions on the joint (i.e. flexion or extension, rotation, abduction or adduction, side bending). When a myofascial unit is in tension, and presents a limited range of flexibility, or has retractile condition, the myofascial unit will limit the range of motion on that joint on which it has dominance. This increases joint pressure (through coaptation) and facilitates inflammatory process and/or joint degeneration.

To sum up, to achieve maximum efficiency in localized treatment on a joint, it is key to restore the flexibility in the different myofascial units that control that joint. This is why the first step undertaken by the practitioner in treating an affected joint (restricted or painful) will be to assess, and if needed, normalize fascial tension, using the myofascial system treatment method previously mentioned.

When treating articulations it is particularly convenient to set the pattern of vacuum pulses applied with the device as follows:

The TIME UP will be fixed at a value comprised between 0.01 and 0.6 seconds; PULSE LENGTH will be fixed at a value comprised between 0.01 and 2 seconds, the TIME DOWN will be fixed at a value comprised between 0.1 and 2 seconds; and the MAXIMUM VACUUM value will be selected at a value comprised between 40 and 130 mbars taking into consideration the sensitivity of the area to be treated and the patient's tolerance; and the MINIMUM VACUUM value will be fixed at a value (in mbars) within the range of 0% to 45% of the MAXIMUM VACUUM value. The total length of pulse (TIME UP+PULSE LENGTH+TIME DOWN) is normally ranging between 0.03 and 4.6 seconds.

When undertaking treatment of an articulation the practitioner will choose among different alternative treatment options depending on the symptoms presented by the articulation as described below:

If articular oedema is the prevailing symptom, the practitioner should carry out the venous return and lymphatic drainage treatment (described later in the venous return and lymphatic drainage system section).

If the prevailing symptoms are one or more of pain, limited range of motion or typical symptoms of degenerative processes a localized treatment is carried out on the articulation and its periphery. The treatment should start with the application of the vacuum stimulus to the articulation held in a relaxed position.

After treatment of the articulation in the relaxed position, the practitioner evaluates whether the range of motion of the articulation has ameliorated. To do this the practitioner mobilizes the bone (or bones) or the joint under assessment, testing movements of flexo-extension, rotation, abduction and adduction, side bending etc. (depending of the bone and joint under assessment).

In the case that the previous treatment with the joint in the relaxed position has not ameliorated the range of motion of the joint the practitioner will change the status of the joint from the initial relaxed position to a slightly stretched position and repeat the treatment described above. Again at the end of the treatment the practitioner evaluates whether there has been an amelioration and if this is not the case proceed to further increase the degree of stretch of the joint and repeat the treatment as many times as necessary.

This iterative procedure allows the application of the vacuum stimulus at different levels of stretch and achieves greater efficiency thereby generating immediate beneficial effects such as an increase in range of motion/flexibility of the joint.

Treatment of Connective Tissue

In the case that the treatment is applied to the connective tissue a stimulation of the tissue is achieved which results in an improvement of the retractile process (or non-elastic) of the connective tissue. This improvement enables patients to recover movement in fascia, in aponeurosis and in articulations that had lost their elastic properties; manifesting in retractions in the connective tissue system, with limited elasticity (whether due to age, training, overuse, repetitive movements or previous injury), a loss that was considered normal and is commonly considered irreversible.

The following treatment protocol is effective in recuperating the elasticity of the connective tissue system:
TIME UP is fixed at a value comprised between 0.2 and 0.3 seconds;
PULSE LENGTH is fixed at a value comprised between 0.5 and 0.6 seconds
TIME DOWN is fixed at a value comprised between 0.2 and 0.3 seconds
MAXIMUM VACUUM is fixed at a value comprised between 60 and 100 mbars.
MINIMUM VACUUM value is fixed at a value of 0 mbar.

The total length of pulse (TIME UP+PULSE LENGTH+TIME DOWN) is normally ranging between 0.9 and 1.2 seconds.

The total wave time is between 3 and 4 minutes and the total treatment time is between 3 and 4 minutes.

To be effective the treatment needs to be applied over the whole area of the connective tissue under treatment.

An example of this treatment in described in EXAMPLE 4.

Treatment of Venous System

As previously explained the treatment by applying a variable vacuum stimulus to the area in need of such treatment is particularly valuable when treating the lesion or lesions located along a tensional chain.

Nevertheless it is also possible to apply variable vacuum stimulus to treat problems of the venous system such as venous stenosis of any origin (muscular, connective tissue system, post-surgery fibrosis), venous insufficiency (and pain associated to it), dilated veins (varicose, spider/broken veins), insufficiency or dysfunction of venous valves and oedema or fluid retention due to insufficiency. When treating problems of the venous system the practitioner will proceed in two separate stages: a first step to reduce venous stenosis and a second step to drain fluids. Two of the most notable problems of the venous systems that may be treated are venous stenosis and problems of venous drainage as described below:

Venous Stenosis.

It has been found that the existence of myofascial or connective tissue under tension is often an underlying cause of venous stenosis thereby reducing the efficiency of drainage, creating venous insufficiency and/or reducing the functioning of the local valves. It has also been found that certain areas of dense miofascial and connective tissue are particularly prone to cause stenosis on local veins when being unduly tensioned. These areas are the following:

a) Internal and posterior region of the knee; great saphenous vein, minor saphenous vein, popliteal vein.

b) Scarpa's triangle and saphenous hiatus; femoral vein, great saphenous vein, circumflex iliac vein, superficial epigastric vein, superficial external pudendal vein, accessory saphenous vein.

c) Anterior, lateral and internal region of the ankle; the veins in the foot.

d) Muscle and fascia of the adductor major, adductor longus, sartorious, vastus medialis, hiatus of the adductor major, anteromedial intermuscular septum; femoral vein.

e) Subclavicular space; Subclavicular and cephalic vein.

f) Axillary region and anterior part of the shoulder; axillary and cephalic vein.

g) Anterior region of the elbow; cephalic and basilic vein.

h) Anterior and posterior region of the carpal bone; veins in the hand.

i) Region comprising the masseter muscle and fascia, inferior region of the ear, muscle and fascia of the sternocleidomastoid and platysma muscle; internal, external and anterior jugular vein, fascial veins, superficial temporal veins, posterior auricularis veins, retromandibular, angular, supraorbitary and infraorbitary veins.

Thus, when a patient presents a dysfunction in the venous system, the practitioner will carry out a treatment on the areas of dense connective and myofascial tissue to reduce the venous stenosis using the variable vacuum stimulus as described above for the treatment of the myofascial system. It has been found that the application of the variable vacuum stimulus successfully reduces stenosis of the veins in the treated region. As a result, venous return, oedema, inflammation and valve function is also improved.

When treating venous stenosis it is particularly convenient to set the pattern of vacuum pulses applied with the device as follows:
The TIME UP will be fixed at a value comprised between 0.01 and 3 seconds; PULSE LENGTH will be fixed at a value comprised between 0.01 and 15 seconds, the TIME DOWN will be fixed at a value comprised between 0.01 and 2 seconds; and the MAXIMUM VACUUM value will be selected at a value comprised between 20 and 200 mbars taking into consideration the sensitivity of the area to be treated and the patient's tolerance; and the MINIMUM VACUUM value will be fixed at a value (in mbars) within the range of 0% to 30% of the MAXIMUM VACUUM value. The total length of pulse (TIME UP+PULSE LENGTH+TIME DOWN) is normally ranging between 0.03 and 20 seconds.

Venous Drainage

The treatment is performed by applying at the region of the vein that is more distal with respect to the associated area of dense connective tissue a vacuum stimulus consisting of 1-8 pulses with a total wave time between 0.3 and 1.4 seconds each pulse. Then, the applicator is displaced stepwise between 0.5 and 10 cm in the direction of the centre of the dense connective tissue and a vacuum stimulus consisting of 1-8 pulses is applied after each displacement until the central point of the dense connective tissue is reached. The whole process may be repeated up to a maximum of 10 times for a total treatment time of 15 to 70 minutes depending on the number veins to be treated.

When treating venous stenosis it is particularly convenient to set the pattern of vacuum pulses applied with the device as follows:

The TIME UP will be fixed at a value comprised between 0.01 and 0.6 seconds; PULSE LENGTH will be fixed at a value comprised between 0.01 and 0.5 seconds, the TIME DOWN will be fixed at a value comprised between 0.1 and 0.6 seconds; and the MAXIMUM VACUUM value will be selected at a value comprised between 20 and 100 mbars taking into consideration the sensitivity of the area to be treated and the patient's tolerance; and the MINIMUM VACUUM value will be fixed at a value (in mbars) within the range of 0% to 10% of the MAXIMUM VACUUM value. The total length of pulse (TIME UP+PULSE LENGTH+TIME DOWN) is normally ranging between 0.12 and 1.7 seconds.

Treatment of Lymphatic System

It is also possible to apply variable vacuum stimulus to treat problems of the lymphatic system such as lymphatic insufficiency, primary or secondary lymphoedema and pain caused by lymphatic fluid retention.

It has been observed that post-surgical fibrotic scar tissue and/or tension in the connective and myofascial system may cause an obstruction in the lymphatic system (stenosis on the lymphatic ducts and/or lymphatic nodes thereby causing oedema, inflammation and/or swelling When treating problems of the lymphatic system the practitioner will proceed in two separate stages: a first step consisting in the treatment of groups of lymph nodes to reduce stenosis therein and a second step to drain fluids from the symptomatic lymphatic ducts.

Treating Groups of Lymph Nodes

Thus, when a patient presents a dysfunction in the lymph system, the practitioner will carry out a treatment on the groups of lymph nodes to reduce the stenosis using the variable vacuum stimulus as described above for the treatment of the myofascial system. It has been found that the application of the variable vacuum stimulus successfully reduces stenosis of the lymph nodes in the treated region. As a result the normal function of the lymphatic ducts is restored allowing a correct drainage.

When treating groups of lymph nodes it is particularly convenient to set the pattern of vacuum pulses applied with the device as follows:

The TIME UP will be fixed at a value comprised between 0.01 and 3 seconds; PULSE LENGTH will be fixed at a value comprised between 0.01 and 15 seconds, the TIME DOWN will be fixed at a value comprised between 0.01 and 2 seconds; and the MAXIMUM VACUUM value will be selected at a value comprised between 20 and 200 mbars taking into consideration the sensitivity of the area to be treated and the patient's tolerance; and the MINIMUM VACUUM value will be fixed at a value (in mbars) within the range of 0% to 30% of the MAXIMUM VACUUM value. The total length of pulse (TIME UP+PULSE LENGTH+TIME DOWN) is normally ranging between 0.03 and 20 seconds.

Lymphatic Ducts Drainage

The treatment is performed by applying at the region of the lymph duct that is more distal with respect to the associated group of lymph nodes, a vacuum stimulus consisting of 1-8 pulses. Then the applicator is displaced stepwise between 0.5 and 10 cm in the direction of the centre of the dense connective tissue and a vacuum stimulus consisting of 1-8 pulses is applied after each displacement until the central point of the dense connective tissue is reached. The whole process may be repeated up to a maximum of 10 times for a total treatment time of 15 to 70 minutes.

When performing drainage of the lymphatic ducts it is particularly convenient to set the pattern of vacuum pulses applied with the device as follows:

The TIME UP will be fixed at a value comprised between 0.01 and 0.6 seconds; PULSE LENGTH will be fixed at a value comprised between 0.01 and 0.5 seconds, the TIME DOWN will be fixed at a value comprised between 0.1 and 0.6 seconds; and the MAXIMUM VACUUM value will be selected at a value comprised between 20 and 110 mbars taking into consideration the sensitivity of the area to be treated and the patient's tolerance; and the MINIMUM VACUUM value will be fixed at a value (in mbars) within the range of 0% to 10% of the MAXIMUM VACUUM value. The total length of pulse (TIME UP+PULSE LENGTH+TIME DOWN) is normally ranging between 0.12 and 1.4 seconds.

Treatment of Microcirculation

Finally it has been found that it is also possible to apply variable vacuum stimulus to activate microcirculation of fluids in the extracellular space and in the blood vessels. The activation of microcirculation is associated with a number of beneficial effects such as the activation of the transport of oxygen, $CO_2$, nutrients (glucose, sodium, potassium, vitamins . . . ), electrolytes in the extracellular space, the improvement of cellular interchange, the improvement of cellular metabolism, the increase of the electrical potential of the membrane, the improvement of cell and tissue regeneration and the drainage of extracellular toxic metabolic waste.

When treating microcirculation it is particularly convenient to set the pattern of vacuum pulses applied with the device as follows:

The TIME UP will be fixed at a value comprised between 0.01 and 0.3 seconds; PULSE LENGTH will be fixed at a value comprised between 0.01 and 0.5 seconds, the TIME DOWN will be fixed at a value comprised between 0.1 and 0.6 seconds; and the MAXIMUM VACUUM value will be selected at a value comprised between 50 and 140 mbars taking into consideration the sensitivity of the area to be treated and the patient's tolerance. The total length of pulse (TIME UP+PULSE LENGTH+TIME DOWN) is normally ranging between 0.12 and 1.4 seconds.

The treatment is performed by applying to the area in which it is desired to activate microcirculation a variable vacuum stimulus as shown in FIG. 14. During PULSE LENGTH the suction stretches, compacts and squeezes the tissue that is receiving the force of the suction through the applicator, the pressure on the tissue is transmitted to the extracellular space and local vessels, generating a mobilization of extracellular liquid and microcirculation in the vessels. During the RELAXATION TIME the vacuum is reduced to a value close to zero or in the alternative a negative vacuum (positive pressure) up to 40 mbars is applied and the microcirculation moves once again through osmosis. Thus, the variable vacuum stimulus generates a pump effect on the extracellular space and microcirculation, the stimulus is similar to the action of an active muscle; a combination of contraction (PULSE LENGTH) and relaxation (RELAXATION TIME). The pulse (contraction-relaxation) has to be quick (the quicker the pulse rate, the more stimulated the microcirculation). If it is pain free for the patient a pulse rate of more than one stimulus per second is preferably used.

The present diagnostic and treatment method has been found useful for the diagnosis and treatment of conditions related to the skeletal muscle system, such as acute muscle tension (contraction), chronic muscle tension (contraction), muscle pain, muscle fibrosis, muscle atrophy; conditions related to the fascia system, such as acute and chronic fascia tension, acute and chronic retractile processes, myo- and interfascial adhesions, myo- and interfascial oedema, fibrosis of the fascial system, compartment syndrome, nerve hiatus stenosis, venous hiatus stenosis, arterial hiatus stenosis, lymphatic vessel hiatus stenosis, capsulitis; conditions related to the vascular system, such as venous stenosis, arterial stenosis, ischemia, hypoxia, varicose veins, cellulite, oedema; conditions related to the lymphatic system, such as stenosis of the lymphatic node and vessels system, lymphatic retention, lymphoedema; conditions related to the joint system, such as lumbago, backache, neck pain, pelvic and sacroiliac joint pain, coxalgia, coxofemoral joint pain, patellofemoral pain, knee joint pain, foot pain, scapular pain, glenohumeral pain, acromioclavicular pain, clavico-sternal pain, costocondral pain, costosternal pain, sternoxiphoid joint pain, costotransverse joint pain, atlanto-occipital joint pain, elbow pain, carpal pain, hand pain, hand pain, cranial suture pain, temporomandibular pain, tendon pathology (tendinitis, tendosynovitis, etc.), flexor retinaculum pathology (carpal tunnel syndrome, etc.), synovial pathology, ligament pathology, limiting of joint movements, increase in articular coaptation, intra and peri-articular oedema, degenerative joint pathology, arthropathy; conditions related to the nervous system, such as neuropathic pain, hyperaesthesia, hypoaesthesia, nerve stenosis, peridural stenosis, perinerve stenosis, nerve stenosis caused by articular pressure, nerve stenosis caused by muscle tension, nerve stenosis caused by fascia system pressure, nerve degeneration, post-surgical fibrosis, ischemia, hypoxia, perinerve, endonerve and epinerve oedema, perinerve fibrosis and other miscellaneous conditions such as fibromyalgia, carpal tunnel syndrome, post-surgical fibrosis, urinary and faecal incontinence, benign prostatic hypertrophy, impotence, anorgasmia, dyspareunia, dry vagina, myofibromas, uterine polyps, endometriosis, constipation, flatulence, inhibition of intestinal peristaltism, intestinal colic-pain, asthma, acute and chronic bronchitis, chronic pharyngitis, eyestrain, cervical tinnitus, vertigo, capsular contracture caused by breast implants, fibrosis caused by burns and whiplash injury.

Treatment of Fibrosis and/or Adhesions

The description below contains the details for the treatment of fibrosis and adhesions such as post-surgery fibrosis, fibrotic tissue caused through scar formation, post fibre rupture reconstruction and/or infection and the presence of adhesion between tissue planes.

The following effective and pain free treatment of fibrosis and adhesions seeks to give a bio-stimulus to the fibrosis in order to generate a change in the elasticity of the fibrotic tissue, to restore range of movement, restore tissue elasticity, reduce neurovascular stenosis, reduce pain and increase vascularization in the area.

Fibrosis responds well to treatment with the application of a combination of two kinds of stimulus:
1. Short pulse stimulus (short total length of pulse)
2. Long pulse stimulus (long total length of pulse), preferably combined with localized maneuvers carried out by the practitioner).

The treatment begins with the application of short pulse stimulus program followed by a long pulse stimulus program with maneuvers. A description of the two treatments follows:

Short Pulse Stimulus (Short Total Length of Pulse)

The treatment enables the application of a massage action using a vacuum stimulus consisting of relatively short pulses having a total length of pulse between 0.5 and 2 seconds and a MAXIMUM VACUUM between 20 and 150 mbars (the intensity of the vacuum will be selected depending on the sensitivity of the fiber). The total wave time on a given fibrotic area is comprised between 1 and 7 minutes.

The best efficacy in fibrosis treatment appears when applying vacuum using the following parameters:
TIME UP is fixed at a value comprised between 0.2 and 0.3 seconds;
PULSE LENGTH is fixed at a value comprised between 0.4 and 0.5 seconds
TIME DOWN is fixed at a value comprised between 0.2 and 0.3 seconds
MAXIMUM VACUUM is fixed at a value comprised between 30 and 100 mbars taking into consideration the sensitivity of the area to be treated and the patient's tolerance: Initially it is set at 100 mbars. If the patient does not report any painful sensation the treatment is continued at this value. If the patient reports pain during the treatment the MAXIMUM VACUUM is reduced in steps of 10 mbars until no pain is reported. No pain has ever been reported at MAXIMUM VACUUM LEVELS of 30 mbars.
MINIMUM VACUUM value is fixed at a value (in mbars) within the range of 0% to 30% of the MAXIMUM VACUUM value.

The total length of pulse (TIME UP+PULSE LENGTH+ TIME DOWN) is normally ranging between 0.8 and 1.1 seconds.

The stimulus generated on the fibrotic tissue by the treatment improves flexibility and colour and reduces hardness, thickness, pain and inflammation of this tissue and generates a recovery of the orientation of the collagen fibrils involved in the remodeling and improvement of the scar tissue fibrosis. This effect is also seen in the deep layers (at periosteum level).

Detailed Treatment Procedure

The applicators are placed on the scar and the vacuum stimulus is applied (total wave time). Once the stimulus is over, the applicators are moved (0.1-2 cm) along from the fulcrum point following the trajectory of the scar. The more apparent the fibrosis, the smaller the distance moved. The applicators are shifted after each wave of pulses, until treatment has been administered on the whole area of the scar.

The treatment on the scar can be applied between 1-8 times, as needed.

The size of the head used in the first treatment step is important as there should be no pain caused during the treatment; small heads (between 1 and 42 cm$^2$) are used for this. Once the first treatments have been administered and no pain has been reported by the patient, applicators of a larger size may be used (between 1 and 110 cm²).

The periphery of the scar/fibrosis also needs to be treated; this can be done either before or after the treatment on the scar. The same stimulus and procedure is used as for the treatment of the scar.

An example of this treatment in described in EXAMPLE 3.

Effects:

The purpose of the suction massage stimulus is to generate a combination of stretch-relaxation on the fibrotic fiber. Numerous stimuli are generated per minute (between 130 and 30 stimuli per minute) because the time between these stimuli is short. The different effects are:
1. A positive bio-stimulus on the fibrosis, allowing the fibrosis to become more pliable; it becomes more elastic and thus reduces the capacity of stenosis (a key feature of this process)
2. The stretch stimulus on the planes and the massage on the adhesions/fibrosis may generate detachment or rupture of the adhesions and/or fibrosis.
3. Stimulus to the fibroblast can stimulate the production of elastin, generating a progressive change of fibrotic fibre toward pliable fibre.
4. The use of short trapezium time with a high number of pulsations per minute (between 120 and 30 stimuli per minute) has a major stimulatory effect on the vascular and lymphatic system draining localized oedema and increasing vascularisation. Pain relief is swift and recovery is quicker and more effective.

Long Pulse Stimulus (Long Total Length of Pulse)

The second treatment step involves the application of long pulse stimulus having a total length of pulse between 2.1 and 15 seconds. During the duration of each pulse the practitioner can execute stretch maneuvers on the fibrosis (in the same way described in the section "Localized treatment with maoeuvers") of the myofascial system.

As described there; during each pulse the practitioner can stretch the fibrosis and mobilize the planes under the scar in 8 directions to decide which direction/s present limitations (because of adhesion/fibrosis). Once the restriction is localized, the practitioner executes the maneuver treatment.

The best efficacy in treatment for releasing any adhesion/fibrosis between any affected plane (fascia, aponeurosis, myofascial, perineural, bone, tendon, ligament, nerve etc.) is achieved using vacuum stimuli defined through the following parameters:

TIME UP is fixed at a value comprised between 0.2 and 1 second;
PULSE LENGTH is fixed at a value comprised between 5 and 15 seconds
TIME DOWN is fixed at a value comprised between 0.2 and 1 second
MAXIMUM VACUUM is fixed at a value comprised between 60 and 140 mbar.
MINIMUM VACUUM value is fixed at 0 mbar.

The total length of pulse (TIME UP+PULSE LENGTH+TIME DOWN) is normally ranging between 5.4 and 17 seconds.

While the vacuum stimulus is at its maximum value maximum suction is exerted on the tissue thereby stretching the underlying planes. It is during this time that the practitioner maneuvers the applicator head and thus stretches the tissue planes further. These maneuvers help mobilize the adhered planes in order to release the adhesions present between the different planes.

Treatment frequency and treatment duration: 1 to 5 treatments per week can be applied. When only one treatment a week is applied the duration of the treatment time is longer; between 40 and 75 minutes. If there are 2-5 treatments a week treatment time per treatment is lower; between 15 and 35 minutes.

An example of this treatment in described in EXAMPLE 5.

Action

The above described treatment generates a bio-stimulus on the fibrotic area that helps detaching or breaking the fibers present between the two tissue planes. These effects help recover the movement between the tissue planes, make the scar tissue more flexible and reduce the stenosis that the fibrosis has produced in the other tissues.

While the second step of the treatment (application of long pulse stimuli) has lesser effect on the vascular and lymphatic system compared to the treatment with the short trapezium time, it has a greater effect on gaining elasticity in the fibrosis and detaching adhesions between larger planes

EXAMPLES

Example 1: How to Identify and Interpret the Injury Chain Arising in the Right Ischiotibial Muscle A patient has been suffering from lumbar pain in vertebral joints L3, 4, 5 and in the right and left paravertebral muscles for the past 2 years. The practitioner observes a right posterior injury chain in the right paravertebral muscle; the injury chain continues along the right gluteus maximus and continues to the right ischiotibial muscle. The next links in the chain are the calves, but they are not suffering from tension. Therefore the link in the most caudal position (the lowest one) is the right ischiotibial muscle: this is what causes the injury chain (it is the one that constitutes the "primary lesion" or "site of origin" in the injury chain. Consequently if the right ischiotibial muscle is not released, the kinetic chain on the lumbar region will not disappear.

According to the Saló-Darder method, the interpretation is that the patient has an injury chain which starts in the right ischiotibial muscle and causes an injury chain in two regions: in the bone area and in the part of the connective joint of the fascia to the gluteus maximus. Let's take a detailed look at each of these regions.

With respect to the bone area, it should be remembered that the ischiotibial muscle is inserted into the knee joint and the iliac bone (ischium); when the ischiotibibial muscle is in tension it pulls the iliac bone, favouring iliac retroversion. The latter movement generates an incorrect movement of the sacrum, causing an imbalance at the base that supports the spine. In turn, the movement of the iliac bone produces compensatory tension in the muscles of the lumbar region and iliac crest (paravertebral muscles and lumbar quadrate muscles).

With regard to the fascia system, it should be borne in mind that the ischiotibial and gluteus maximus muscle fascia have a union (the hinge joint) where the movement is made jointly by both of them, entwined in a myofascial chain. The ischiotibial tension thus produces tension on the fascia and the gluteus maximus muscle, which, due to being inserted into the sacrum and posterior iliac crest, exercises an unstable kinetic chain on the biomechanics of the sacrum and pelvis and the antagonist muscles and fascia system of the tension exerted by the gluteus maximus and its fascia are in tension, in order to rebalance the pelvic-lumbar mechanical tension. The result is an imbalance in the spinal column.

This situation leads to constant tension (chronic) on the lumbar region, which is the reason why local treatment on the lumbar region has no effect. Thus, once the practitioner has relieved the tension in the right ischiotibial and right gluteus maximus, the injury chain will disappear and the tension balance on the pelvis, sacrum and spine will be restored. When the injury chain has been eliminated, the practitioner can apply local treatment to the painful lumbar region, which is much more effective.

Example 2: Application of the Treatment Method to Patients Suffering from Chronic Neck Pain A study was conducted in which the Fisium device was used on 20 patients with chronic neck pain.

Figure 1:
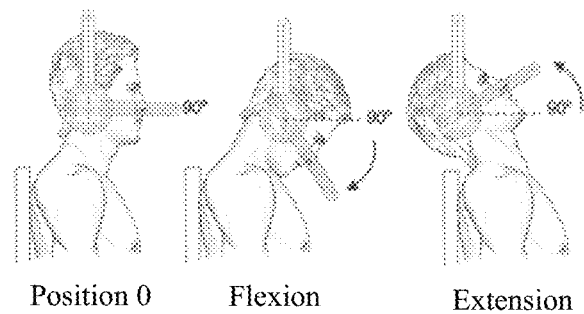
FIG. 1 illustrates the flexion and extension movements used by the practitioner to evaluate the state of a patient's neck.
Figure 2:
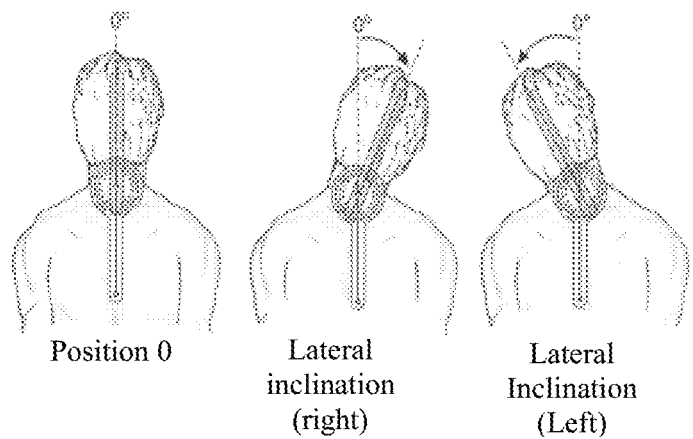
FIG. 2 illustrates the inclination movements (tilting to the left and to the right) used by the practitioner to evaluate the state of a patient's neck.
Figure 3:
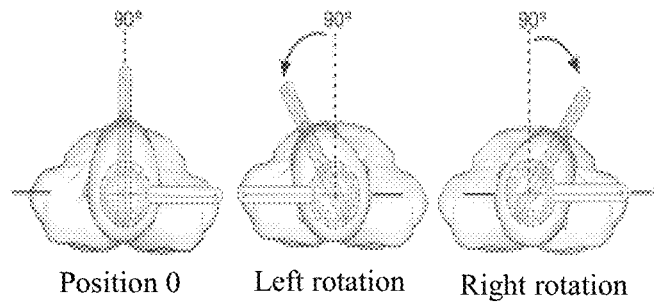
FIG. 3 illustrates the rotation movements used by the practitioner to evaluate the state of a patient's neck.

The state of the patient before and after treatment was evaluated using two groups of parameters:
1. Movement parameters (flexion and extension as illustrated in FIG. 1; tilting of head to the right and left as illustrated in FIG. 2 and right and left rotation as illustrated in FIG. 3).
2. Pain level measured in accordance with the VAS (Visual Analogue Scale).

Figure 6:
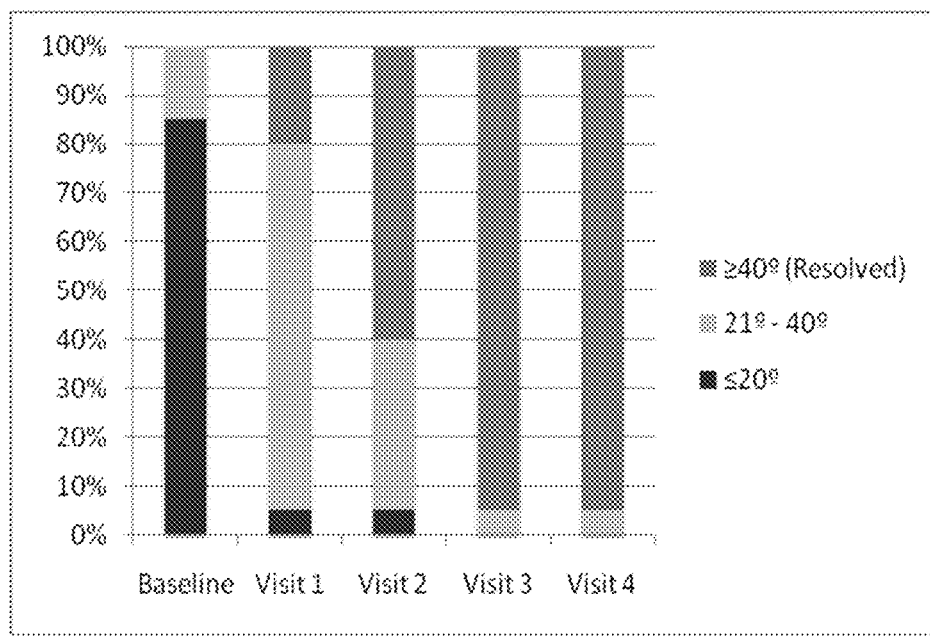
FIG. 6 illustrates the improvement in the degree of tilting to the right (measured in degrees) achieved by patients after 1 to 4 visits during which treatment was received.
Figure 7:
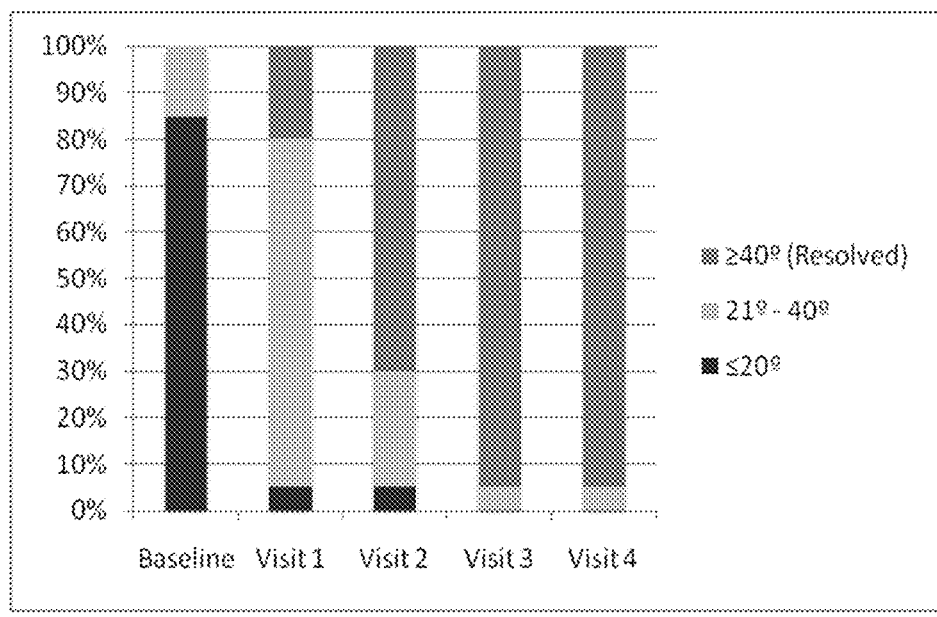
FIG. 7 illustrates the improvement in the degree of tilting to the left (measured in degrees) achieved by patients after 1 to 4 visits during which treatment was received.

The treatment was effected by applying negative pressure (vacuum using the device shown in FIGS. 11 and 12, which correspond to FIGS. 6 and 7 of WO 2011/101388, which is hereby incorporated by reference herein in its entirety. In FIGS. 11 and 7 an embodiment of a skin treatment assembly 200 is shown. The treatment assembly 200 comprises a suction machine 100 and a support device 10.

The suction machine 100 comprises a housing 150 provided with wheels 155 at the base thereof for ease of moving. Control means 160 are also provided for controlling certain treatment parameters such as length, pressure, applicator position, etc. Control means 160 include output means comprising a display screen 161 through which the practitioner is allowed to control treatment. A keyboard can be provided for entering treatment parameters and selecting a mode of treatment. The display screen 161 is fitted at one end of a mount arm 162. The mount arm 162 is attached, at the opposite end thereof, to the suction machine housing 150. There may be embodiments in which the control means 160 are fitted in the support device 10 instead of the suction machine 100 such that it is nearer to the practitioner.

Suction means 120 are provided within the housing 150 of the suction machine 100. Suction means 120 may comprise a vacuum pump suitable for applying different pressurized airflow patterns (for example, pressure changing values every 0.1-0.5 s) to a patient through applicators 110.

The support device 10 comprises a connecting member 30 that is displaceably mounted on a support member 11. Base portion 12 is formed of a series of supporting arms 13 each carrying a dual wheel carpet caster 14. The wheeled base portion 12 allows the support device 10 to be easily moved in the proximity of a patient's body for a suitable positioning for a skin treatment. Alternatively, the base portion can be fixed. The support device 10 further comprises an arm structure 20. The arm structure 20 of the support device 10 is pivotally coupled to the connecting member 30 through a substantially horizontal first axis. Rotation of the arm structure 20 to the connecting member 30 and displacement (upwards/downwards) of the connecting member 30 along the support member 11 allows the relative vertical position of the arm structure 20 to be accurately adjusted. Said relative vertical position is defined as the height of applicators 110 to the ground.

The carrying structure 40 of the arm structure 20 further comprises a carrying bar 45 that can be adapted for receiving a corresponding hose connector 50, 60. Each hose connector 50, 60 is provided with one inlet 70 and one outlet 80. The inlet 70 is provided with a movable joint 71 that is adapted for receiving at least one negatively pressurized air inlet hose 90 that conducts negatively pressurized air from a suction machine 100 to the support device 10. The outlet 80 of the hose connectors 50, 60 may be also provided with a corresponding movable joint 81 adapted for receiving at least one pressurized air outlet hose 96, 97. Said outlet hoses 96, 97 lead to respective applicators 110. With this arrangement, several modes of treatment can be used, for example including either the supply of the same pressure values through all the outlet hoses 96, 97 or the supply of different negative pressure values through said outlet hoses 96, 97 according to the treatment requirements.

The treatment of patients was effect by applying a variable pattern of negative pressure defined through the following parameters: TIME UP=0.2 seconds; PULSE LENGTH=0.5 seconds; TIME DOWN=0.3 seconds; RELAXATION TIME=0.1 seconds; MINIMUM VACUUM=0 mbars; MAXIMUM VACUUM=100 mbars (for patients whose age is comprised between 14- and 50 years), 90 mbars (for patients whose age is comprised between 51 and 60 year old) and 80 mbars (for patients older than 60 year old).

The treatment consists is performed in 5 phases:
1. The right and left posterior tensional chains are relaxed placing the heads along posterior pelvic, lumbar and thoracic zones. 8 zones are treated simultaneously with the adjustable fixed arms; 4 treatment series of 3 minutes each (12 minutes in total) are applied; after each treatment, the heads are shifted to apply dosage on untreated zones. The position of the applicators (110) during treatment is illustrated in FIGS. 21 and 22.

2 Localized treatment to scapular muscles (suprapinal, trapezius and rhomboids, Levatator scapulae; etc.) using mobile arms. These muscles belong to the RPTC or LPTC (depending on the side), and transverse scapular potential tensional (TSTC) chains. After 4 or 6 pulses, the therapist shifts the applicators (110) 3 cms along the treatment zone. Treatment total time: 14 minutes. The position of the applicators (110) during treatment is illustrated in FIGS. 23 and 24.

3. The therapist proceeds to treat cervical muscles (belonging to RPTC and LPTC). After 4 or 6 pulses, the therapist shifts the applicators (110) 3 cms along the treatment zone. Treatment total time: 7 minutes. The position of the applicators (110) during treatment is illustrated in FIGS. 25 and 26.

4. The therapist proceeds to treat the cervical anterior and lateral myofascial units belonging to both medial (RMTC and LMTC) and lateral (RLTC and LLTC) tensional chains. After 4 or 6 pulses, the therapist shifts the applicators (110) 3 cms along the treatment zone. Treatment total time: 8 minutes. The position of the applicators (110) during treatment is illustrated in FIG. 27.

5. The therapist assesses the range of mobility and performs localized treatment to treat painful points, adhesions, adhesion in planes, tension, retractile processes, spasticity, oedema and haematoma local to the muscular and/or fascial group. After 4 or 6 pulses, the therapist shifts the applicators 3 cms along the treatment zone. Treatment total time: 8 minutes. The position of the applicators (110) during treatment is illustrated in FIG. 28.

Figure 4:
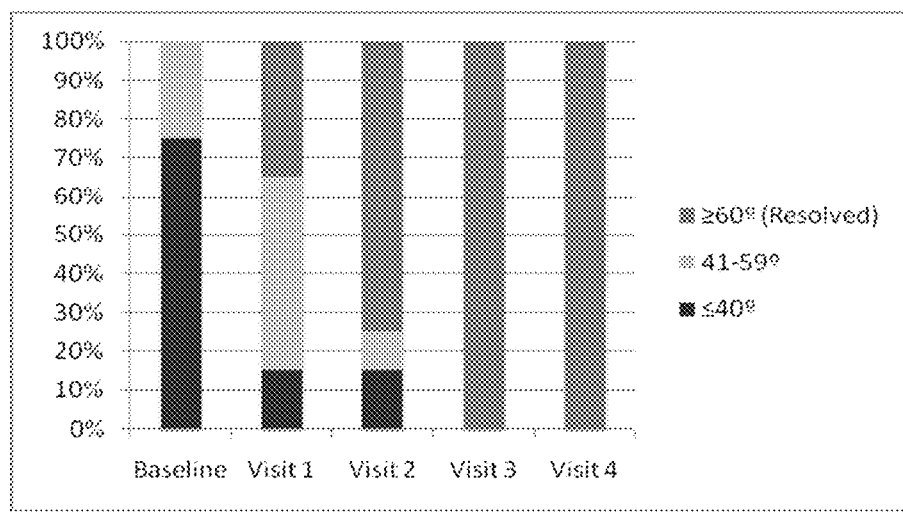
FIG. 4 illustrates the improvement in the degree of flexion (measured in degrees) achieved by patients after 1 to 4 visits during which treatment was received.

The results of the study are summarised in the following charts and graphs:

FIG. 1: Flexion and extension of the head.
FIG. 2: Tilting of head to the right and left.
FIG. 3: Right and left rotation of the head.
FIG. 4: Improvement in the degree of flexion achieved by patients.

Patients were classified in three groups according to their capacity to flex the head:
 Group 1: Patients who were unable to flex the head more than 40°
 Group 2: Patients who were able to flex the head between more than 41° and 59°
 Group 3: Patients who were able to flex the head at least 60° (considered healthy)

The figure shows the percentage of patients in each group before starting treatment and after 1, 2, 3 and 4 treating sessions. It may be seen that from the third session all patients treated could be considered healthy.

Figure 5:
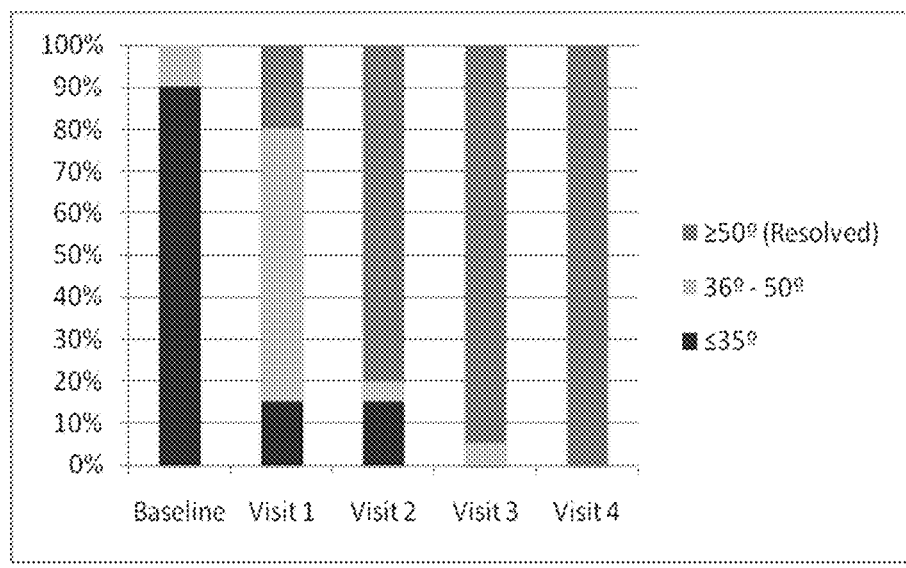
FIG. 5 illustrates the improvement in the degree of extension (measured in degrees) achieved by patients after 1 to 4 visits during which treatment was received.

FIG. 5: Improvement in the degree of extension achieved by patients.

Patients were classified in three groups according to their capacity to extend the head:
 Group 1: Patients who were unable to extend the head more than 35°
 Group 2: Patients who were able to extend the head between more than 36° and 49°
 Group 3: Patients who were able to extend the head at least 50° (considered healthy)

The figure shows the percentage of patients in each group before starting treatment and after 1, 2, 3 and 4 treating sessions. It may be seen that from the third session practically all patients treated could be considered healthy.

FIG. 6: Improvement in the degree of tilting to the right achieved by patients.

Patients were classified in three groups according to their capacity to tilt the head to the right:
 Group 1: Patients who were unable to tilt the head to the right more than 20°
 Group 2: Patients who were able to tilt the head to the right between more than 21° and 39°
 Group 3: Patients who were able to tilt the head to the right at least 40° (considered healthy)

The figure shows the percentage of patients in each group before starting treatment and after 1, 2, 3 and 4 treating sessions. It may be seen that from the third session practically all patients treated could be considered healthy.

FIG. 7: Improvement in the degree of tilting to the left achieved by patients.

Patients were classified in three groups according to their capacity to tilt the head to the left:
 Group 1: Patients who were unable to tilt the head to the left more than 20°
 Group 2: Patients who were able to tilt the head to the left between more than 21° and 39°
 Group 3: Patients who were able to tilt the head to the left at least 40° (considered healthy)

The figure shows the percentage of patients in each group before starting treatment and after 1, 2, 3 and 4 treating sessions. It may be seen that from the third session practically all patients treated could be considered healthy.

Figure 8:
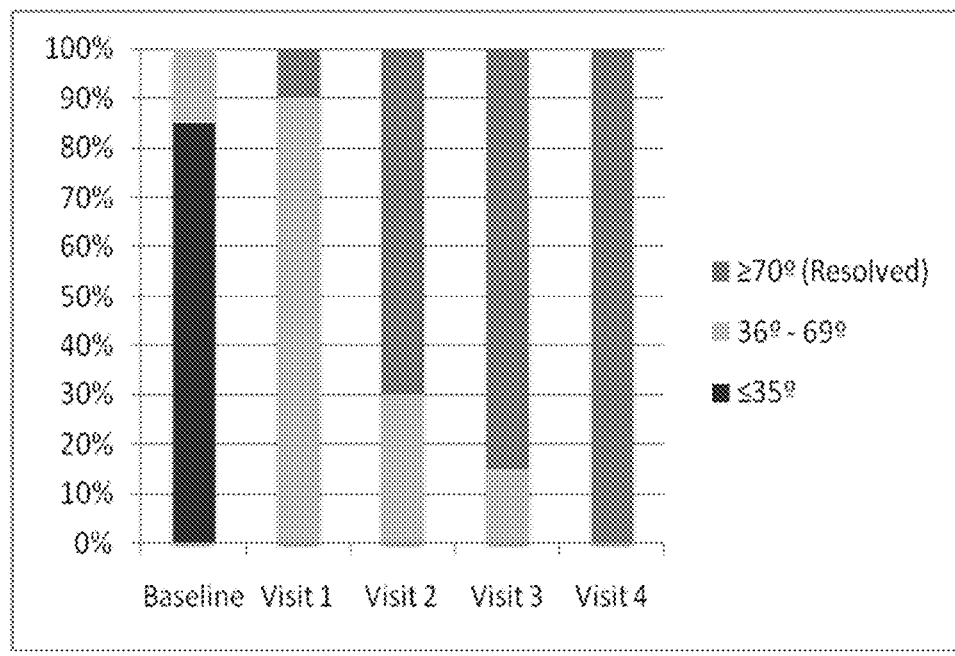
FIG. 8 illustrates the improvement in the degree of rotation to the right (measured in degrees) achieved by patients after 1 to 4 visits during which treatment was received.

FIG. 8: Improvement in the degree of rotation to the right achieved by patients.

Patients were classified in three groups according to their capacity to rotate the head to the right:
 Group 1: Patients who were unable to rotate the head to the right more than 35°
 Group 2: Patients who were able to rotate the head to the right between more than 36° and 69°
 Group 3: Patients who were able to rotate the head to the right at least 70° (considered healthy)

The figure shows the percentage of patients in each group before starting treatment and after 1, 2, 3 and 4 treating sessions. It may be seen that from the fourth session practically patients treated could be considered healthy.

Figure 9:
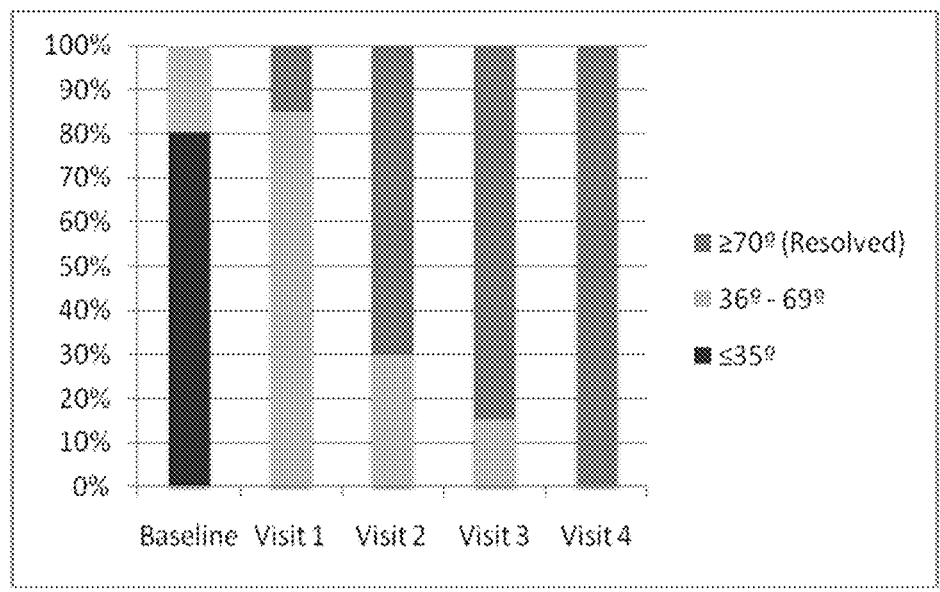
FIG. 9 illustrates the improvement in the degree of rotation to the left (measured in degrees) achieved by patients after 1 to 4 visits during which treatment was received.

FIG. 9: Improvement in the degree of rotation to the left achieved by patients.

Patients were classified in three groups according to their capacity to rotate the head to the left:
 Group 1: Patients who were unable to rotate the head to the left more than 35°
 Group 2: Patients who were able to rotate the head to the left between more than 36° and 69°
 Group 3: Patients who were able to rotate the head to the left at least 70° (considered healthy)

The figure shows the percentage of patients in each group before starting treatment and after 1, 2, 3 and 4 treating sessions. It may be seen that from the fourth session practically patients treated could be considered healthy.

FIG. 10: VAS Score during treatment

FIG. 10 illustrates the distribution of patients according to their VAS score (Visual Analogue Scale) at the first visit/treating session, the second visit/treating session, the third visit/treating session and the forth visit/treating session.

The VAS score or Visual Analogue Scale is a score commonly used to evaluate the intensity of pain suffered by patients.

To determine the VAS Score the patient is shown a scale from 0 to 10 (such as the one illustrated in FIG. 29) wherein a score of 0 indicates no pain, scores of 1 to 3 indicate a mild pain (nagging, annoying, interfering little with activities of daily living), scores of 4 to 6 indicate moderate pain (interferes significantly with activities of daily living) and scores of 7 to 10 indicate severe pain (disabling; unable to perform activities of daily living) and is asked to indicate the number that would best describe his level of pain. This number is the VAS Score for the patient.

It is observed that from the third visit, pain reduction among patients was quite significant. From the fourth visit, the pain disappeared completely in all the patients.

Example 3: This Example Shows a Successful Treatment of a Patient Reporting Pain in a Scar Produced by a Surgical Intervention Medical history: A 60 year old patient, operated on an inguinal hernia on the left side, 12 months previously. Patient reports pain in the zone of a scar produced by a surgical intervention. The scar is painful upon palpation and the pain (VAS 8) was associated with a worsening of the movement and stretching evaluation.

Assessment:
 a) Displacement of superficial fascia; there is NO movement in the superficial fascias (presence of adhesions).

Description of treatment: Since the underlying cause of the muscle tension and the limitation in myofascial mobility is the existence of post-surgical fibrosis a treatment of fibrosis and adhesions was applied as follows:

A 40 minutes session treatment has been applied once a week. After three sessions pain had disappeared:

Session 1:
a) Application of Short Pulse Vacuum Stimuli with the Following Parameters:
TIME UP was fixed at 0.2 seconds;
PULSE LENGTH was fixed at 0.4 seconds
TIME DOWN was fixed at 0.3 seconds
MAXIMUM VACUUM was fixed at a value of 60 mbars
MINIMUM VACUUM was fixed at a value of 0 mbars The total length of pulse (TIME UP+PULSE LENGTH+TIME DOWN) was 0.9 seconds.

The total wave time at each position of the applicator heads was 1.50 min.

Two 17 cm$^2$ applicators were placed on the scar, one where the scar began and the other one in the center of the scar. The vacuum stimulus described above was applied during 1 minute and 30 seconds. Throughout the duration of the treatment the applicators were not moved from the area. Once the total wave time had ended the applicators were moved 1 cm along the line of the scar and the vacuum stimulus was applied again (1 min 30 sec). This was repeated until the whole of the scar had been treated (the applicator which was at the beginning of the scar ended up in the middle and the applicator which began in the middle of the scar will have been moved to the end of the scar. To cover the whole area of the scar 5 series of vacuum stimuli need to be administered (total treatment time 7.5 minutes).

Next, the applicators were changed to ones of a larger diameter (42 cm$^2$). One applicator was placed at the beginning of the scar and the other one at the center of the scar. The vacuum stimulus was applied for a total wave time of 1 minute and 30 seconds. Throughout the duration of the treatment the applicators were not moved from the area. Once the total wave time had ended the applicators were moved 1 cm along the line of the scar and the vacuum stimulus was applied again. (1 min 30 sec). This was repeated until the whole of the scar had been treated (the applicator which was at the beginning of the scar ended up in the middle and the applicator which began in the middle of the scar will have been moved to the end of the scar. To cover the whole area of the scar 5 treatments needed to be administered (total treatment time 7.5 minutes).

After the above treatment the fibrosis improved and the scar became less rigid and less sensitive to touch.
b) Application of Long Pulse Stimuli with the Following Parameters.
TIME UP was fixed at 1 second;
PULSE LENGTH was fixed at 8 seconds
TIME DOWN was fixed at 1 second
MAXIMUM VACUUM was fixed at a value of 70 mbars
MINIMUM VACUUM was fixed at a value of 0 mbars The total length of pulse (TIME UP+PULSE LENGTH+TIME DOWN) was 10 seconds.

The total wave time was 10 seconds (the wave consisted of a single pulse).

The total treatment time at each position of the applicator heads was 15 min.

A 42 cm$^2$ applicator was used. The applicator was placed at the beginning of the scar; the practitioner maneuvered the applicator and the tissue being treated in a northward direction during the "pulse length" (8 seconds). The objective of the maneuver was to stretch the different planes of the tissues that had post surgery fibrosis and adhesions. During "time down", the practitioner moved the applicator 1 cm along the scar and repeated this process until the whole length of the scar had been covered. Once all the northward maneuvers were completed, the practitioner repeated the process in a southward direction, then in an eastward direction and finally in a westward direction. It took 10 minutes to complete all the maneuvers.

Once the maneuvers on the fibrosis were completed the practitioner assessed the movement or non-movement of the fibrotic tissue. To do this, the practitioner displaced the tissue under the applicator in 8 directions (north, northeast, east, southeast, south, southwest, west and northwest) during the "pulse length" cycle. This was made to determine whether or not the tissue moved correctly or presented limitation when moved. The patient presented a limitation in the westward direction. Having determined that the limitation was in the westward direction, maneuvers were carried out to release the adhesions to regain normal movement. During "Pulse length" (8 seconds) the practitioner maneuvered the applicator in a westward direction to stretch the fibres present in these planes, when the "Pulse length" finished and during "Time down" the practitioner moved the applicator 1 cm and repeated the maneuver until the treatment had covered the entire area of the affected tissue under treatment. On termination of the preceding treatment it was found that the maneuvers had been insufficient to change the fibrotic tissue and so the treatment was repeated. However, after the second treatment of maneuvers on the fibrosis there was a notable improvement in the tissue with over 50% increased mobility in the hypodermis and underlying planes. A treatment time of 5 minutes was needed.
Session 2:
a) Application of Short Pulse Vacuum Stimuli with the Following Parameters:

The treatment was the same as in session 1, except for an increase of 10 mbar in the MAXIMUM VACUUM which was possible because the patient's scar was less painful after session 1:
TIME UP was fixed at 0.2 seconds;
PULSE LENGTH was fixed at 0.4 seconds
TIME DOWN was fixed at 0.3 seconds
MAXIMUM VACUUM was fixed at a value of 70 mbars
MINIMUM VACUUM was fixed at a value of 0 mbars The total length of pulse (TIME UP+PULSE LENGTH+TIME DOWN) was 0.9 seconds.

The total wave time at each position of the applicator heads was 1.50 min.

The total treatment time was 27 min.
b) Application of Long Pulse Stimuli with the Following Parameters.

The treatment was the same as in session 1, except for an increase of 10 mbar in the MAXIMUM VACUUM which was possible because the patient's scar was less painful after session 1
TIME UP was fixed at 1 second;
PULSE LENGTH was fixed at 8 seconds
TIME DOWN was fixed at 1 second
MAXIMUM VACUUM was fixed at a value of 80 mbars
MINIMUM VACUUM was fixed at a value of 0 mbars The total length of pulse (TIME UP+PULSE LENGTH+TIME DOWN) was 10 seconds. The total wave time was 10 seconds (the wave was constituted by a single pulse).

The total treatment time was 13 min.
Session 3:
a) Application of Short Pulse Vacuum Stimuli with the Following Parameters:

The treatment was the same as in session 2, except for an increase of 10 mbar in the MAXIMUM VACUUM which was possible because the patient's scar was less painful after session 2:
TIME UP was fixed at 0.2 seconds;
PULSE LENGTH was fixed at 0.4 seconds TIME DOWN was fixed at 0.3 seconds
MAXIMUM VACUUM was fixed at a value of 80 mbars
MINIMUM VACUUM was fixed at a value of 0 mbars The total length of pulse (TIME UP+PULSE LENGTH+TIME DOWN) was 0.9 seconds.

The total wave time at each position of the applicator heads was 1.50 min. The total wave time was 10 seconds (the wave was constituted by a single pulse).

The total treatment time was 28 min.

b) Application of Long Pulse Stimuli with the Following Parameters.

The treatment was the same as in session 2, except for an increase of 10 mbar in the MAXIMUM VACUUM which was possible because the patient's scar was less painful after session 2:
TIME UP was fixed at 1 second;
PULSE LENGTH was fixed at 8 seconds
TIME DOWN was fixed at 1 second
MAXIMUM VACUUM was fixed at a value of 90 mbars
MINIMUM VACUUM was fixed at a value of 0 mbars The total length of pulse (TIME UP+PULSE LENGTH+TIME DOWN) was 10 seconds. The total wave time was 10 seconds (the wave was constituted by a single pulse).

The total treatment time was 12 min.

The results obtain after the three treatment sessions described above could be summarized as follows:

a) After treatment the patient presented a Grade 0 muscle tension in iliopsoas and adductor muscles and NO pain on palpation.

b) After treatment the patient presented Grade 0 presents miofascial mobility limitation in the iliopsoas and adductor muscles.

c) After treatment the patient presented NO adhesions in the superficial fascias which had full mobility.

Example 4: This Example Shows a Successful Treatment of a Patient Reporting Pain and Limited Coxofemoral Movement in the Right Leg Not Associated with a Degenerative Articular Process Medical history: A 40 year old patient presents a 10 month old pain and limited coxofemoral movement in the right leg (35° limitation in medial rotation). The screening tests exclude the existence of a degenerative articular process
Assessment:
a) Muscle tension: the patient presents Grade 3 muscle tension in the right gluteus maximus and piriformis muscle (pain elicited on palpation)
b) Miofascial mobility: The patient presents Grade 3 limitation in the right gluteus maximus and piriformis muscle
c) Displacement of superficial fascia; The patient's superficial fascias have no movement denoting the presence of adhesions.

Description of treatment: A treatment directed to the recovery of the connective tissue associated with the articulation was applied. A 60 minutes session was applied once a week until the range of movement was normalized. Normal rotation was achieved after four sessions.
Dosage Strength Used in the Four Sessions and Improvement Achieved in the Range of Movement.
Session 1:
a) First, inhibition treatment was carried out. The patient was asked to lie in prone position on a treatment table with a 15 cm thick pillow under his feet. The practitioner placed the applicators over the whole extension of the gluteus maximus. Six applicator heads, each of 72 cm² were positioned in two parallel lines of three. A first series of vacuum stimuli was applied for a total wave time of 3 minutes. After the application of this first series of stimuli the practitioner moved all the applicator heads 3 cm towards the head and a new series of stimuli was applied for another total wave time of 3 minutes. After this second series the practitioner moved once more the applicator heads 3 cm towards the head and repeated the 3 minute treatment. After having applied the above mentioned 3 series of vacuum stimuli the practitioner moved the applicators outwards 3 cm and administered another 3 minute treatment. Then, the practitioner moved the applicators 3 cm towards the feet and administered a new 3 minute treatment. Once completed, the applicators were once again moved 3 cm towards the feet and the last 3 minute treatment was applied. In total, 6 series of vacuum stimuli (as described below) were applied for a total of 18 minutes covering the whole area of the gluteus maximus and piriformis muscle (which lies under the gluteus maximus) with the muscle in a relaxed position (inhibition).

For the above mentioned series of vacuum stimuli the parameters were fixed as follows:
TIME UP was fixed at 0.3 seconds;
PULSE LENGTH was fixed at 0.5 seconds
TIME DOWN was fixed at 0.3 second
MAXIMUM VACUUM was fixed at a value of 80 mbars
MINIMUM VACUUM was fixed at a value of 0 mbars The total length of pulse (TIME UP+PULSE LENGTH+TIME DOWN) was 1.1 seconds.

b) The next treatment step was an inhibition and stretch treatment carried out on the affected myofascial unit (gluteus maximus, piriformis). The patient was asked to stay in the same position (lying prone). The practitioner used a mobile arm with a 72 cm² applicator and holds the tibia and the fibula with his free hand. The practitioner positioned the head over the sacrum where the muscles to be treated insert and for 8 pulse stimuli did not move the applicator while keeping the coxofemoral joint externally rotated (inhibition). After the eighth pulse stimulus the leg was slowly and progressively rotated internally (thus stretching the muscles under treatment) to their stretch limit. Meanwhile, with the applicator head still in position the practitioner continued administering the treatment dose. At the end of the stretch, the practitioner kept the applicator in position and administered a further 8 pulse stimuli. Then, the leg was slowly rotated externally and returned to the initial position. Once the inhibition-stretch cycle was completed, the practitioner moved the applicator and repeated the procedure until the whole length of the muscle had been treated. The total treatment time was 10 minutes.

For the above mentioned series of vacuum stimuli the parameters were fixed as follows:
TIME UP was fixed at 0.3 seconds;
PULSE LENGTH was fixed at 0.5 seconds
TIME DOWN was fixed at 0.3 second
MAXIMUM VACUUM was fixed at a value of 80 mbars
MINIMUM VACUUM was fixed at a value of 0 mbars The total length of pulse (TIME UP+PULSE LENGTH+TIME DOWN) was 1.1 seconds.

c) The above mentioned treatment caused a great change at the pelvis level: the pelvis presented itself as being blocked in retroversion. Thus, a compensatory treatment was carried out on the entire vertebral column to ease its adaptation to the new position of the pelvis. The stimuli were applied to the entire area of the paravertebral lumbar muscles, in 4 series of vacuum stimuli (as described below) and total treatment time was 12 minutes.

For the above mentioned series of vacuum stimuli the parameters were fixed as follows:

TIME UP was fixed at 0.3 seconds;
PULSE LENGTH was fixed at 0.5 seconds
TIME DOWN was fixed at 0.3 second
MAXIMUM VACUUM was fixed at a value of 80 mbars
MINIMUM VACUUM was fixed at a value of 0 mbars
The total length of pulse (TIME UP+PULSE LENGTH+TIME DOWN) was 1.1 seconds.
The patient showed no improvement in rotation at 8 days after the first session.
Session 2:
The treatment was the same as in session 1, except for an increase of 10 mbar in the
The patient showed an improvement of 10° in rotation at 8 days after the first session leaving the limitation in medial rotation to a value of 25°
Session 3:
The treatment was the same as in session 2, except for an increase of 10 mbar in the
The patient showed an improvement of 15° in rotation at 8 days after the first session leaving the limitation in medial rotation to a value of 10° (compared to an initial limitation of 35°).
The results obtain after the three treatment sessions described above could be summarized as follows:
After treatment the patient presented a Grade 0 muscle tension in the right gluteus maximus and piriformis muscle.
After treatment the patient miofascial mobility at the right gluteus maximus and piriformis muscle showed no limitation.

Example 5: This Example Shows a Successful Treatment of a Patient Reporting Pain in the in the Internal Area of the Left Knee Medical history: A 35 year old patient presenting pain (VAS 7) in the internal area of the left knee. Problem originated 3 months ago with a history of injury. Diagnostic screening has not found any of the tissues to be ruptured. The practitioner found adhesions in the area of pain (internal capsule of the knee). In the painful area, the tissue does not move during the sliding maneuver over the tissue planes and presents sticking/adhesion from the hypodermis level to the deeper tissue planes
Description of treatment: A treatment consisting of the application of stretch to zone where adhesions are present was applied. The treatment involved a 30 minutes session once a week applying vacuum stimuli. The pain disappeared after two 30 minutes sessions.
Session 1:
A series of vacuum stimuli were applied characterized by the following parameters:
TIME UP was fixed at 1 second;
PULSE LENGTH was fixed at 8 seconds
TIME DOWN was fixed at 1 second
MAXIMUM VACUUM was fixed at a value of 100 mbars
MINIMUM VACUUM was fixed at a value of 0 mbars
The total length of pulse (TIME UP+PULSE LENGTH+TIME DOWN) was 10 seconds.
The total wave time was 10 seconds (the wave was constituted by a single pulse).
The total treatment time was 10 min.
The patient showed an improvement in the pain sensation (VAS=3 after the first session).
Session 2:
The treatment was the same as in session 1, except for an increase of 20 mbar in the MAXIMUM VACUUM and the duration of the treatment:
TIME UP was fixed at 1 second;
PULSE LENGTH was fixed at 8 seconds
TIME DOWN was fixed at 1 second
MAXIMUM VACUUM was fixed at a value of 120 mbars
MINIMUM VACUUM was fixed at a value of 0 mbars
The total length of pulse (TIME UP+PULSE LENGTH+TIME DOWN) was 10 seconds. The total wave time was 10 seconds (the wave was constituted by a single pulse).
The total treatment time was 20 min.
The patient showed a complete remission of the pain sensation (VAS=0 after the first session).

Example 6: Treatment of Adhesions and Scar Tissue Fibrosis

Medical history: 60 year old patient, operated on an inguinal hernia on the left side, 12 months previously. Patient reports pain at the operation site, worsening with movement and stretching (VAS 8); the scar is painful upon palpation.
Assessment:
a) Muscle tension: presents grade 3 muscle tension in the iliopsoas and adductor muscles (pain elicited on palpation)
b) Myofascial mobility: presents grade 3 limitation in iliopsoas and adductor muscles.
c) Displacement of superficial fascia; there is NO movement in the superficial fascias (presence of adhesions).
Description of Treatment:
A one week 40 minutes session treatment is applied. After three sessions pain disappeared
Session 1:
TIME UP was fixed at 0.2 second;
PULSE LENGTH was fixed at 0.4 seconds
TIME DOWN was fixed at 0.3 second
MAXIMUM VACUUM was fixed at a value of 60 mbars
MINIMUM VACUUM was fixed at a value of 0 mbars
The total length of pulse (TIME UP+PULSE LENGTH+TIME DOWN) was 0.9 seconds.
The total wave time at each position of the applicator heads was 1.5 min.
The total treatment time was 7.5 min.
Two 17 cm$^2$ applicators were placed on the scar, one where the scar begins and one in the middle of the scar. The above described protocol was used for a total wave time of 1 minute and 30 seconds. Throughout the duration of the wave the applicators were not moved from the area where they were initially applied. Once the wave time has ended the applicators are moved 1 cm along the line of the scar and the treatment is applied again (1 min 30 sec). This is repeated until the whole extension of the scar has been treated (the applicator which was at the beginning of the scar ended up in the middle and the applicator which began in the middle of the scar had been moved to the end of the scar. To cover the whole area of the scar 5 treatments were needed (total treatment time 7.5 minutes).
Then, the applicators were changed to applicators of a larger area (42 cm$^2$). One applicator was placed at the beginning of the scar and the other in the middle. The above-mentioned protocol was applied for a total wave time of 1 minute and 30 seconds. Throughout the duration of the treatment the applicators were not moved from the area where they were initially applied. Once the wave time has ended the applicators were moved 1 cm along the line of the scar and the treatment was applied again for another 1 min 30 sec. This process was repeated until the whole extension of the scar had been treated (the applicator which was at the beginning of the scar ended up in the middle and the applicator which began in the middle of the scar had been moved to the end of the scar. To cover the whole area of the scar 5 treatments were needed (total treatment time 7.5 minutes).

After the treatment described above the fibrosis showed a clear improvement; it is less hard and is less sensitive to touch.

b) Next, long pulse stimuli (with associated maneuvers to treat adhesions and fibrosis in the different planes) are applied.
TIME UP was fixed at 1 second;
PULSE LENGTH was fixed at 8 seconds
TIME DOWN was fixed at 1 second
MAXIMUM VACUUM was fixed at a value of 70 mbars
MINIMUM VACUUM was fixed at a value of 0 mbars The total length of pulse (TIME UP+PULSE LENGTH+TIME DOWN) was 10 seconds.

The total wave time was 10 seconds.

The total treatment time was 15 minutes

A 42 cm² applicator is used. The applicator was placed at the beginning of the scar; practitioner maneuvered the applicator and the tissue being treated in a northward direction during the "pulse length" (8 seconds). The objective was to stretch the different planes of the tissues that have post surgery fibrosis and adhesions. After the total wave time, the practitioner moved the applicator 1 cm along the scar and repeated the process until the whole length of the scar had been covered.

Once all the northward maneuvers are completed, the practitioner repeated the process in a southward direction, then in an eastward direction and finally in a westward direction. It took 10 minutes to complete all the maneuvers.

Once the maneuvers on the fibrosis are completed the practitioner assessed whether the fibrotic tissue was movable. To do this, the practitioner displaced the tissue under the applicator in 8 directions (north, northeast, east, southeast, south, southwest, west and northwest) during the "pulse length" cycle. This was done to determine whether or not the tissue was able to move correctly or presented limitations when moved. The assessment showed that the patient presented a limitation in the westward direction. Having determined the limitation was in the westward direction, maneuvers were carried out to release the adhesions to regain normal movement. During the total wave time (10 seconds) the practitioner maneuvered the applicator in a westward direction to stretch the fibres present in these planes, After the "total wave time" the practitioner moved the applicator 1 cm and repeated the maneuver until the treatment had covered the entire area of the affected tissue under treatment. On termination of the preceding treatment it was found that the maneuvers had been insufficient to change the fibrotic tissue and so the treatment was repeated. However, after the second treatment of maneuvers on the fibrosis there was a notable improvement in the tissue with over 50% increased mobility in the hypodermis and underlying planes. A treatment time of 5 minutes was needed.

Session 2: Dosage Strength Increased a) First, short pulse stimuli were applied. As the patient reported less pain than in the previous sesión the "Maximum vacuum" strength was increased by 10 mbars. For the rest the treatment was the same as in session 1, the only difference being a 10 mbar increment in order to attain greater depth and generate a greater biostimulus in the fibrotic tissue.
TIME UP was fixed at 0.2 second;
PULSE LENGTH was fixed at 0.4 seconds
TIME DOWN was fixed at 0.3 second
MAXIMUM VACUUM was fixed at a value of 70 mbars
MINIMUM VACUUM was fixed at a value of 0 mbars The total length of pulse (TIME UP+PULSE LENGTH+TIME DOWN) was 0.9 seconds.

The total wave time at each position of the applicator heads was 1.5 minutes.

b) Next, long pulse stimuli (with associated maneuvers for treating fibrosis and adhesions between planes) were applied. The treatment was similar to the one applied during the second phase of sesión 1. The strength of "Maximum vacuum" was further increased by 10 mbars to a total of 80 mbars. A treatment time of 13 minutes was applied.
TIME UP was fixed at 1 second;
PULSE LENGTH was fixed at 8 seconds
TIME DOWN was fixed at 1 second
MAXIMUM VACUUM was fixed at a value of 80 mbars
MINIMUM VACUUM was fixed at a value of 0 mbars The total length of pulse (TIME UP+PULSE LENGTH+TIME DOWN) was 10 seconds.

The total wave time at each position of the applicator heads was 1.5 minutes.

Session 3: dosage strength and treatment time increased a) First, short pulse stimuli were applied.
TIME UP was fixed at 0.2 seconds;
PULSE LENGTH was fixed at 0.4 seconds
TIME DOWN was fixed at 0.3 seconds
MAXIMUM VACUUM was fixed at a value of 80 mbars
MINIMUM VACUUM was fixed at a value of 0 mbars The total length of pulse (TIME UP+PULSE LENGTH+TIME DOWN) was 0.9 seconds.

The total wave time at each position of the applicator heads was 1.5 minutes.

A treatment time of 7.5 min was applied.

b) Next, long pulse stimuli (with associated maneuvers for treating adhesions between planes) were applied.
TIME UP was fixed at 1 second;
PULSE LENGTH was fixed at 8 seconds
TIME DOWN was fixed at 1 second
MAXIMUM VACUUM was fixed at a value of 90 mbars
MINIMUM VACUUM was fixed at a value of 0 mbars The total length of pulse (TIME UP+PULSE LENGTH+TIME DOWN) was 10 seconds.

The total wave time at each position of the applicator heads was 10 seconds.

The total treatment time was 12 minutes.

Pain was assessed 8 days after the last one of the 3 session described above using the VAS scale (shown in FIG. 29) and a value of zero (0) was obtained, i.e. the patient reported no pain.

The status of the affected zone (the scar) was assessed by a practitioner as herein above described and the following results were obtained:

Muscle tension: presents muscle tension Grade 0 in iliopsoas and adductor muscles. (NO pain on palpation).

Miofascial mobility: presents Grade 0 limitation in the iliopsoas and adductor muscles.

Displacement of superficial fascias: there is mobility in the superficial fascias; there are NO adhesions present.

Example 7: Recovery of the Elastic Properties of the Connective Tissue

The example described below illustrates the beneficial effect of a treatment according to the invention when applied to the connective tissue system, wherein the elasticity of the connective tissue is restored. This improvement enables patients to recover movement in fascia, in aponeurosis and in articulations that had lost their elastic properties (due to age, training, overuse, repetitive movements, previous injury or otherwise), a loss that was considered normal and is commonly considered irreversible.

Medical History: 40 year old patient presenting a 10 month old pain and limited coxofemoral movement in the right leg (presents 35° limitation in medial rotation); screening tests exclude a degenerative articular process.

Assessment:

Muscle tension: presents Grade 3 muscle tension in the right gluteus maximus and piriformis muscle (pain elicited on palpation)

Miofascial mobility: Presents Grade 3 limitation in the right gluteus maximus and piriformis muscle.

The treatment methodology described in above for the treatment of the muscle and fascia system is used on the myofascial system of the gluteus maximus and piriformis in order to recuperate movement in the connective tissue and the muscle.

The treatment is applied, following the protocol described below, once a week in 60 minutes session, until the range of movement is normalized; normal rotation is achieved after four treatments. To be effective the treatment was applied over the whole area of the connective tissue under treatment.

Session 1:

a) First, inhibition treatment was carried out on the affected myofascial unit. The patient was made to lie in prone position on the treatment table with a 15 cm pillow under his feet. The practitioner placed the fixed arm applicators over the whole extension of the gluteus maximus (inferiorly from the sacrum passing over the area of the ischium and superiorly from the gluteus medius to the insertion of the femur): six 72 cm$^2$ applicator heads were applied and were positioned in two parallel lines of three.

The area was treated under the following protocol:
TIME UP was fixed at 0.3 seconds;
PULSE LENGTH was fixed at 0.5 seconds
TIME DOWN was fixed at 0.3 second
MAXIMUM VACUUM was fixed at a value of 80 mbars
MINIMUM VACUUM was fixed at a value of 0 mbars The total length of pulse (TIME UP+PULSE LENGTH+TIME DOWN) was 1.1 seconds.

The total wave time at each position of the applicator heads was 3 min

After the application of the first wave for a total wave time of 3 min the practitioner moved all the applicators 3 cm towards the head and a second wave was administered. After administration of the second wave was finished the practitioner once again moved the applicators 3 cm towards the head and administered a third 3 minutes wave. After administration of the third wave was finished the practitioner once again moved the applicators 3 cm towards the head and administered a fourth 3 minutes wave. After administration of the third wave was finished the practitioner moved the applicators 3 cm towards the feet and administers a fifth 3 minute wave. Once completed, the applicators were once again moved 3 cm towards the feet and the last 3 minute wave was applied. In total, 6 waves of pulses were administered for a total treatment time of 18 minutes covering the whole area of the gluteus maximus and piriformis muscle (which lies under the gluteus maximus) with the muscle in a relaxed position (inhibition).

b) Then, an inhibition and stretch treatment is carried out on the affected myofascial unit (gluteus maximus, piriformis). The patient remained in the same position (lying prone). The practitioner used a mobile arm with a 72 cm$^2$ applicator and held the tibia and fibula with their free hand. The practitioner positioned the head over the sacrum where the muscles to be treated insert and for 8 pulse stimuli did not move the applicator while keeping the coxofemoral joint externally rotated (inhibition). After the eighth pulse stimulus the leg was slowly and progressively rotated internally (thus stretching the muscles under treatment) to their stretch limit. Meanwhile, with the applicator head still in position the practitioner continued administering the treatment dose. At the end of the stretch, the practitioner kept the applicator in position and administered a further 8 pulse stimuli. Then, the leg was slowly rotated externally and returned to the initial position. Once the inhibition-stretch cycle was completed, the practitioner moved the applicator and repeated the procedure until the whole length of the muscle had been treated. The treatment took 10 minutes.

c) The above mentioned treatment caused an important change in the structure of the pelvis; which was blocked in retroversion. Thus, a compensatory treatment was carried out on the whole of the vertebral column so that it may adapt to the new position of the pelvis. The recuperation of connective tissue programme is applied to the entire area of the paravertebral lumbar muscles for a treatment time 12 minutes.

The patient showed no improvement in rotation at 8 days after the first session.

Session 2: The same treatment procedure as in Session 1 was applied with a 10 mbar increase in "Maximum vacuum".

The area was treated under the following protocol:
TIME UP was fixed at 0.3 seconds;
PULSE LENGTH was fixed at 0.5 seconds
TIME DOWN was fixed at 0.3 second
MAXIMUM VACUUM was fixed at a value of 90 mbars
MINIMUM VACUUM was fixed at a value of 0 mbars The total length of pulse (TIME UP+PULSE LENGTH+TIME DOWN) was 1.1 seconds.

The total wave time at each position of the applicator heads was 3 min.

The patient showed an improvement in medial rotation 8 days after the second session of 10° gain in rotation wherein the initial 35° limitation was reduced to a 25° limitation.

Session 3: The same treatment procedure as in Session 1 was applied, with a 10 mbar increase in "Maximum vacuum" with respect to session 2.

The area was treated under the following protocol:
TIME UP was fixed at 0.3 seconds;
PULSE LENGTH was fixed at 0.5 seconds
TIME DOWN was fixed at 0.3 second
MAXIMUM VACUUM was fixed at a value of 100 mbars
MINIMUM VACUUM was fixed at a value of 0 mbars The total length of pulse (TIME UP+PULSE LENGTH+TIME DOWN) was 1.1 seconds.

The total wave time at each position of the applicator heads was 3 min.

The patient showed an improvement in medial rotation 8 days after the third session of 15° gain in rotation wherein the initial 35° limitation was reduced to a 10° limitation.

Session 4: The same treatment procedure as in Session 1 was applied, with a 10 mbar increase in "Maximum vacuum" with respect to session 3.

The area was treated under the following protocol:
TIME UP was fixed at 0.3 seconds;
PULSE LENGTH was fixed at 0.5 seconds
TIME DOWN was fixed at 0.3 second
MAXIMUM VACUUM was fixed at a value of 110 mbars
MINIMUM VACUUM was fixed at a value of 0 mbars The total length of pulse (TIME UP+PULSE LENGTH+ TIME DOWN) was 1.1 seconds.

The total wave time at each position of the applicator heads was 3 min.

The patient showed an improvement in medial rotation 8 days after the fourth session of 10° gain in rotation wherein the initial 35° limitation was reduced to a 0° limitation.

The status of the affected zone was assessed by a practitioner as herein above described and the following results were obtained:
a) Muscle tension: Presents Grade 0 muscle tension in right gluteus maximus and piriformis muscle.
b) Miofascial mobility: There is no limitation in the right gluteus maximus and piriformis muscle.

Example 8: Removal of Adhesions Between Different Tissue Planes

Medical history: 35 year old patient reporting pain (VAS 7) in the internal area of the left knee. Problem originated 3 months ago with a history of injury. Diagnostic screening has not found any of the tissues to be ruptured. The practitioner found adhesions in the area of pain (internal capsule of the knee). In the painful area, the tissue does not move during the sliding maneuver over the tissue planes and presents adhesion from the hypodermis level to the deeper tissue planes.
Assessment:
Muscle tension: muscle tension Grade 0.
Miofascial mobility: presents Grade 0 limitation.
Superficial fascia displacement: There in NO mobility in the superficial fascias (indicating the presence of adhesions).

A treatment following the procedure outlined above in the section devoted to the treatment of adhesions and scar tissue fibrosis section; combining short pulse stimuli and long pulse stimuli associated with maneuvers, was applied to the painful area and its periphery. A weekly session of 30 minutes was applied. The pain disappeared after the second session.

When the pulse length is administered the applicator head exerts suction on the tissue under it thereby stretching the underlying planes. During this time the practitioner maneuvers the applicator head to increase the angle of stretch of the underlying tissue planes. These maneuvers mobilize the under-adhered planes and help release the adhesions present between the different planes.

Dosage used in the two sessions and pain improvement achieved:
Session 1:
a) First, short pulse stimuli were applied to the painful area. This was done with the patient lying supine on the treatment bed. The practitioner placed two applicators (one of 42 cm² and the other of 25 cm²) on the painful area via the fixed arms. A first wave was applied to relax the articular connective tissue, improve pliability of the adhesions and prime the area for the subsequent treatment of releasing the adhesions.
TIME UP was fixed at 0.2 seconds;
PULSE LENGTH was fixed at 0.4 seconds
TIME DOWN was fixed at 0.3 second
MAXIMUM VACUUM was fixed at a value of 100 mbars
MINIMUM VACUUM was fixed at a value of 0 mbars
The total length of pulse (TIME UP+PULSE LENGTH+ TIME DOWN) was 0.9 seconds.
The total wave time at each position of the applicator heads was 1.5 min.

A first 1.5 min wave was applied and then the applicators were displaced 2 cm and a further 1.5 min wave was applied to the new area. The process was repeated 3 more times so that in total 5 waves were applied covering all the affected area. Thus, the total treatment time to cover the whole area of the tissue under treatment was 7 minutes and 30 seconds.

b) As a second step, a treatment to release the adhesions is administered. The treatment consisted in the application of waves formed by long pulse stimuli with the simultaneous application of maneuvers by the practitioner to release adhesions with the following protocol:
TIME UP was fixed at 1 second;
PULSE LENGTH was fixed at 8 seconds
TIME DOWN was fixed at 1 second
MAXIMUM VACUUM was fixed at a value of 100 mbars
MINIMUM VACUUM was fixed at a value of 0 mbars
The total length of pulse (TIME UP+PULSE LENGTH+ TIME DOWN) was 10 seconds.

The practitioner used a 42 cm² applicator to apply the vacuum waves and to carry out the maneuvers for releasing adhesions. The maneuvers carried out by practitioner during the time of the "pulse length" were as follows; the practitioner displaced the tissue underneath the applicator in 8 directions (north, northeast, east, southeast, south, southwest, west and northwest) to assess whether the tissue moves or whether it presents limitations upon displacement. The latter would confirm the presence of adhesions. In this case, the patient presented limited movement in 2 directions (north and south). Having localized the limitation the practitioner carried out maneuvers to release the adhesions. During the "Pulse length" (8 seconds), the practitioner displaced the tissues in a northward direction to stretch the adhesions present in this plane. Once the "Pulse length" ended and during "Time down" the practitioner moved the applicator 1 cm and repeated the treatment, this procedure was repeated until the entire length of the tissue had been treated. Once the treatment of releasing adhesions in the northward direction was concluded it was repeated in a southward direction. These two treatments (maneuvers to release tissue north and south) had to be repeated 3 times in this patient, since the first two treatments were not sufficient to achieve to release the adhesions. However, after 3 treatments with maneuvers to remove adhesions the tissue changed notably and movement improved in both the hypodermis and the underlying planes by more than 50%. The total treatment time was 12 minutes.

The patient reported a clear improvement in pain 8 days wherein the VAS score changed from the initial value of 7 to a value of 3.
Session 2:
a) In a first step, waves consisting of short pulse stimuli were applied. The same treatment procedure described for session 1 was applied, with a 10 mbar increment in "Maximum vacuum" with respect to session 1.
TIME UP was fixed at 0.2 seconds;
PULSE LENGTH was fixed at 0.4 seconds
TIME DOWN was fixed at 0.3 second
MAXIMUM VACUUM was fixed at a value of 110 mbars
MINIMUM VACUUM was fixed at a value of 0 mbars
The total length of pulse (TIME UP+PULSE LENGTH+ TIME DOWN) was 0.9 seconds.
The total wave time at each position of the applicator heads was 1.5 min.

b) In a second step waves consisting of long pulse stimuli were applied by the practitioner while simultaneously carrying out maneuvers as described for step b9 in session 1.

The same treatment procedure in session 1 is applied, with a 10 mbar increment in "Maximum vacuum" with respect to session 1.
TIME UP was fixed at 1 second;
PULSE LENGTH was fixed at 8 seconds
TIME DOWN was fixed at 1 second
MAXIMUM VACUUM was fixed at a value of 110 mbars
MINIMUM VACUUM was fixed at a value of 0 mbars The total length of pulse (TIME UP+PULSE LENGTH+ TIME DOWN) was 10 seconds.

The total wave time at each position of the applicator heads was 1.5 min.

The patient reported a clear improvement in pain 8 days wherein the VAS score changed from the value of 3 (reported after session 1) to a value of 0, i.e. the patient reported to be pain-free.

The invention claimed is:

1. A method of treating a tensional myofascial chain the tensional myofascial chain having a plurality of links and dominating an affected area where the patient is reporting symptoms selected from the group of muscular pain, fascial pain, inflammation, limitation of the joint articulation movement, and stenosis in the vascular, lymphatic or nervous systems, the tensional myofascial chain beginning at an asymptomatic primary lesion and ending at a symptomatic lesion distal from the primary lesion, said method comprising;
    (i) identifying which link of the chain is the primary lesion, the primary lesion being the link within the tensional myofascial chain which is in the most caudal position; and,
    (ii) treating the primary lesion by applying a series of vacuum pulses, each of the vacuum pulses representing a series having a trapezoidal form when the vacuum intensity is represented in the Y axis and time is represented in the X axis.

2. The method of claim 1, wherein the primary lesion gives rise to a chronic condition or incorrect structure in myofascial units and associated structures in the human patient.

3. The method of claim 1, wherein the identifying the tensional myofascial chain comprises:
    (i) placing the patient in a position to permit evaluation;
    (ii) anatomically locating an evaluation point to be examined in a link and positioning at least one finger on an evaluation point;
    (iii) observing the direction that the evaluation point moves; and
    (iv) determining if the evaluation point movement is correct or incorrect and the degree of tension in the link being evaluated.

4. The method of claim 3, wherein the position comprises standing, sitting or prone.

5. The method of claim 3, wherein the observation of the direction that the evaluation point moves occurs when the patient stretches fascia.

6. The method of claim 1, further comprising:
    (iii) after the treatment of step (ii) identifying a new primary lesion;
    (iv) treating the new primary lesion;
    (v) repeating steps (ii) and (iv) until no further lesion is detected.

7. The method of claim 1 maintaining between each trapezoidal pulse vacuum at a value different than zero for a predetermined time period.

8. The method according to claim 1, said method further comprising treating at least one other lesion in the chain different from the primary lesion with a treatment step selected from the group of: decontraction of muscle and fascia; relieving tension in muscle and fascia fibers; relaxing sarcomerus; stretching and moving different muscle and fascial planes; and recovery of joint movement parameters.

9. The method according to claim 1, said method further comprising treating the symptomatic lesion distal from the primary lesion.

10. The method according to claim 1, said vacuum stimulus being administered using an apparatus comprising a support device comprising an arm structure associated with a connecting member further comprising at least one hose connector associated with said arm structure and with at least one skin treatment machine applicator, said support device being suitable for maintaining the applicator at a given position when in use.

* * * * *